(12) United States Patent
Pan et al.

(10) Patent No.: US 12,312,398 B2
(45) Date of Patent: May 27, 2025

(54) COMPOSITIONS AND METHODS FOR TARGETING ACTIVIN SIGNALING TO TREAT CANCER

(71) Applicant: The Johns Hopkins University, Baltimore, MD (US)

(72) Inventors: Fan Pan, Baltimore, MD (US); Duojia Pan, Dallas, TX (US); Drew M. Pardoll, Brookeville, MD (US); Joseph Barbi, East Amherst, NY (US); Juan Fu, Lutherville, MD (US); Ying Zheng, Baltimore, MD (US); Andriana Lebid, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 349 days.

(21) Appl. No.: 17/561,496

(22) Filed: Dec. 23, 2021

(65) Prior Publication Data

US 2022/0112279 A1 Apr. 14, 2022

Related U.S. Application Data

(62) Division of application No. 16/077,368, filed as application No. PCT/US2017/017354 on Feb. 10, 2017, now Pat. No. 11,236,156.

(60) Provisional application No. 62/293,915, filed on Feb. 11, 2016.

(51) Int. Cl.
| | |
|---|---|
| *A61K 39/395* | (2006.01) |
| *A61K 31/7105* | (2006.01) |
| *A61K 38/17* | (2006.01) |
| *A61K 39/00* | (2006.01) |
| *A61P 17/06* | (2006.01) |
| *A61P 19/02* | (2006.01) |
| *A61P 35/00* | (2006.01) |
| *C07K 16/22* | (2006.01) |

(52) U.S. Cl.
CPC .......... *C07K 16/22* (2013.01); *A61K 31/7105* (2013.01); *A61K 38/179* (2013.01); *A61K 39/3955* (2013.01); *A61P 17/06* (2018.01); *A61P 19/02* (2018.01); *A61P 35/00* (2018.01); *A61K 2039/505* (2013.01); *A61K 2039/577* (2013.01)

(58) Field of Classification Search
None
See application file for complete search history.

(56) References Cited

U.S. PATENT DOCUMENTS

| | | |
|---|---|---|
| 9,221,915 B2 * | 12/2015 | Belouski ................ A61P 29/00 |
| 11,236,156 B2 | 2/2022 | Pan et al. |
| 2003/0073143 A1 | 4/2003 | Plowman et al. |
| 2009/0234106 A1 | 9/2009 | Han et al. |
| 2010/0279409 A1 | 11/2010 | Robson et al. |
| 2012/0052074 A1 | 3/2012 | Belouski et al. |
| 2014/0220033 A1 | 8/2014 | Han et al. |
| 2015/0132226 A1 | 5/2015 | Greenwood et al. |
| 2017/0306028 A1 | 10/2017 | Knopf et al. |

OTHER PUBLICATIONS

Hardy et al, "The activin A Antagonist Follistatin Inhibits Asthmatic Airway Remodelling," Thorax, 68:1, pp. 9-18, Oct. 10, 2021.
Klages et al., "Selective Depletion of Foxp3 Regulatory T Cells Improves Effective Therapeutic Vaccination Against Established Mellanoma," Cancer Research, 70:20, pp. 7788-7799, Oct. 15, 2010.
Tousa et al., "Actvin-A: a New Piece in the Puzzle of Tolerance in Asthma," retrieved from the Internet: URLhttps://www.ingentaconnect.com/content/ben/caiaad/2014/00000001/00000001/art00007?crawler=true, retrieved on Aug. 14, 2019.
Xuhao Ni et al., YAP is Essential for Treg-Mediated Suppression of Antitumor Immunity, Cancer Discovery, 8:8, pp. 1026-1043, Aug. 1, 2018.
Yoon et al., "Activin Receptor-Like Kinase5 Inhibition Suppresses Mouse Melanoma by Ubiquitin Degradation of Smad4, Thereby Derepressing Eomesodermin in Cytotoxic T Lymphocytes," Embo Molecular Medicine, Wiley-VCH, Weinheim, 5:11, 1720-1739, Nov. 1, 2013.
Stove et al., "Melanoma Cells Secrete Follistatin, an Antagonist of Activin-Mediated growth Inhibition," Oncogene, 23:31, pp. 5330-5339, Apr. 5, 2004.
Antsiferova et al., "Activin Enhances Skin Tumourigenesis and Malignant Progression by Inducing a Pre-Tumourigenic Immune Cell Response," Nature Communications, 2:1, Sep. 1, 2011.
Supplementary European Search Report from Corresponding European Application No. 17750822 dated Aug. 14, 2019, 11 pages.
Huber et al., Activin A Promotes the TGF-beta-Induced Conversion of CD4CD25 T Cells into Foxp3 Induced Regulatory T Cells. The Journal of Immunology, 182: 4633-4640, 2009.
Semitekolou et al., Activin-A induces regulatory T cells that suppress T helper cell immune responses and protect from allergic airway disease. J. Exp. Med. 206 (8): 1769-1785, 2009.
Mougiakakos et al., Regulatory T Cells in Cancer. Advances in Cancer Research 107:57-117, 2010.
International Search Report mailed Jun. 19, 2017 in PCT/US17/17354.
European Office Action mailed Mar. 19, 2024 in EP17750822.3.
Response filed on Jul. 17, 2024 to European Office Action mailed Mar. 19, 2024 in counterpart European application EP17750822.3.

(Continued)

*Primary Examiner* — Ruixiang Li
(74) *Attorney, Agent, or Firm* — Fox Rothschild LLP

(57) ABSTRACT

The present invention relates to compositions and methods for treating cancer by targeting the Activin signaling pathway. In certain embodiments, combining Activin blockade with immunomodulation alters regulatory T (Treg) cell-mediated immune regulation and treats cancer.

10 Claims, 14 Drawing Sheets

(56) References Cited

OTHER PUBLICATIONS

Word-generated Compare document of present U.S. Appl. No. 17/561,496, with text underlined that does not appear verbatim in Applicant's U.S. Appl. No. 62/293,915, filed Feb. 11, 2016.

\* cited by examiner

Foxp3-PE

|  | %Foxp3+ |
|---|---|
| +act./-Tgf-beta | 45.0% |
| +act./+Tgf-beta (0.075 ng/ml) | 60.0% |
| -act./-Tgf-beta | 8.2% |
| -act./+Tgf-beta (0.075 ng/ml) | 43.6% |

COMPOSITIONS AND METHODS FOR TARGETING ACTIVIN SIGNALING TO TREAT CANCER

CROSS REFERENCE TO RELATED APPLICATIONS

This application is a Divisional of U.S. application Ser. No. 16/077,368, filed Feb. 5, 2019, now U.S. Pat. No. 11,236,156, which issued on Feb. 1, 2022, which is a National Stage Application, filed under 35 U.S.C. § 371, of International Application No. PCT/US2017/017354, filed on Feb. 10, 2017, which claims the benefit of priority under 35 U.S.C. § 119 (e) to U.S. Provisional Application No. 62/293,915, filed Feb. 11, 2016, which is incorporated herein by reference in its entirety.

BACKGROUND OF THE INVENTION

Regulatory T cells (Treg) are important for maintaining immune homeostasis; however, in the tumor microenvironment, immunosuppressive Treg cells can hinder effective anti-tumor immune responses and immunotherapies. Therefore, prior to the invention described herein, there was an unmet need for new therapeutic strategies to treat cancer based upon Treg modulation.

SUMMARY OF THE INVENTION

The present invention is based, at least in part, upon the development of methods of treating cancer by targeting Activin signaling to modulate Treg cell function, activity, or proliferation. As described in detail below, antibody-mediated ablation of Activin signaling suppressed the growth of tumors. Additionally, as described herein, inhibition of Activin signaling improved the effectiveness of cell-based anti-tumor vaccines when both are used in combination.

In some cases, increased Treg function, activity, or proliferation can lead to undesirable immunosuppression, thereby preventing immune cell-mediated inhibition of cancer cells. As provided herein, methods of reducing regulatory T cell (Treg) function, activity, or proliferation in a subject are carried out by administering to the subject an effective amount of a composition, e.g., a pharmaceutically effective composition, comprising an Activin signaling modulator, thereby reducing Treg function, activity, or proliferation in the subject. In some cases, the method further comprises identifying the subject as having or at risk of developing increased Treg function, activity, or proliferation. For example, Treg function or activity comprises immune response suppression, i.e., suppression of immune cells that would otherwise mount an immune response against, e.g., a cancer cell. In one aspect, Treg function or activity, e.g., immune response suppression, is reduced by 1%400%, e.g., Treg function or activity is reduced by at least 5%, at least 10%, at least 20%, at least 30%, at least 40%, at least 50%, at least 60%, at least 70%, at least 80%, at least 90%, or 100%. Similarly, Treg proliferation is reduced by 1%-100%, e.g., Treg proliferation is reduced by at least 5%, at least 10%, at least 20%, at least 30%, at least 40%, at least 50%, at least 60%, at least 70%, at least 80%, at least 90%, or 100%. In some cases, the inhibitor is administered to a Treg population in the subject. Preferably, Treg development is inhibited.

The subject is preferably a mammal in need of such treatment, e.g., a subject that has increased Treg function or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

In one aspect, the Activin signaling modulator comprises an Activin antagonist, e.g., an agent which inhibits the function or activity of Activin. For example, the Activin antagonist comprises an Activin inhibitor or an Activin Receptor inhibitor. Alternatively, the Activin antagonist includes an antagonist of a downstream Activin target molecule. Suitable Activin antagonists include an antibody or fragment thereof, a binding protein, a polypeptide, and any combination thereof. In some cases, the Activin antagonist comprises a nucleic acid molecule. Suitable nucleic acid molecules include double stranded ribonucleic acid (dsRNA), small hairpin RNA or short hairpin RNA (shRNA), small interfering RNA (siRNA), or antisense RNA, or any portion thereof. In another aspect, the Activin antagonist comprises an optimized monoclonal anti-Activin A antibody. In another aspect, exemplary Activin antagonists include Follistatin and Follistatin-like 3 (FSRP), which are extracellular proteins that bind Activin irreversibly. In another aspect, a modified propeptide of Activin may bind Activin with high affinity and prevent Activin signaling. In another aspect, Inhibin interferes with the interaction of Activin and its receptor. Other factors are capable of modifying and inhibiting the activity of Activin receptor components such as FK506 binding protein (FKBP12).

In some cases, the antagonist comprises a small molecule. A small molecule is a compound that is less than 2000 Daltons in mass The molecular mass of the small molecule is preferably less than 1000 Daltons, more preferably less than 600 Daltons, e.g., the compound is less than 500 Daltons, less than 400 Daltons, less than 300 Daltons, less than 200 Daltons, or less than 100 Daltons.

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecules can be synthetically engineered to consist of a fragment, or small portion, or a longer amino acid chain to fill a binding pocket of an enzyme. Typically small molecules are less than one kilodalton.

The effective amount of the antagonist (or agonist) is from 0.001 mg/kg to 250 mg/kg body weight, e.g., 0.001 mg/kg, 0.05 mg/kg 0.01 mg/kg, 0.05mg/kg, 1 mg/kg, 5 mg/kg, 10 mg/kg, 25 mg/kg, 50 mg/kg, 75 mg/kg, 100 mg/kg, 125 mg/kg, 150 mg/kg, 175 mg/kg, 200 mg/kg, 225 mg/kg, or 250 mg/kg body weight. Ultimately, the attending physician or veterinarian decides the appropriate amount and dosage regimen.

In some cases, the antagonist (or agonist) is administered at least once per day, at least once per week, or at least once per month. The antagonist (or agonist) is administered for a duration of one day, one week, one month, two months, three months, six months, 9 months, or one year. In some cases, the antagonist (or agonist) is administered daily, e.g., every 24 hours. Or, the antagonist (or agonist) is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours.

In one aspect, the agent is administered orally, intravenously, intramuscularly, systemically, subcutaneously or by inhalation, or by other any method described herein or known to the skilled artisan.

Optionally, the subject has a tumor and the tumor is inhibited or reduced in size following administration, e.g., the tumor size is decreased in size by at least 1%, at least 5%, at least 10%, at least 20%, at least 30%, at least 40%, at least 50%, at least 60%, at least 70%, at least 80%, at least 90%, or 100%

Also provided are methods of treating or preventing cancer in a subject comprising identifying a subject suffering from or at risk of suffering from cancer and administering to the subject an effective amount of a composition comprising an Activin signaling modulator, thereby treating or preventing cancer in a subject. For example, the Activin signaling modulator comprises an Activin antagonist, e.g., an agent which inhibits the function or activity of Activin. For example, the Activin antagonist comprises an Activin inhibitor or an Activin Receptor inhibitor. Alternatively, the Activin antagonist includes an antagonist of a downstream Activin target molecule.

For example, the Activin Receptor comprises ACVR1C (ALK7) and the Activin Receptor inhibitor comprises an antibody. Preferably, the anti-ACVR1C antibody neutralizes ACVR1C. Accordingly, provided are methods of targeting and neutralizing ACVR1C (ALK7) with antibodies to enhance anti-tumor immunity.

Exemplary cancers are selected from the group consisting of carcinoma, sarcoma, tumors, solid tumors, blood cancer, leukemia, lymphoma, skin cancer, melanoma, breast cancer, ovarian cancer, uterine cancer, prostate cancer, testicular cancer, colorectal cancer, stomach cancer, intestinal cancer, bladder cancer, lung cancer, non-small cell lung cancer, pancreatic cancer, renal cell carcinoma, kidney cancer, liver cancer, hepatocarcinoma, brain cancer, head and neck cancer, retinal cancer, glioma, lipoma, throat cancer, thyroid cancer, neuroblastoma, endometrial cancer, myeloma, and esophageal cancer. One suitable type of cancer which is treated using the methods described herein is melanoma.

In some cases, the method further comprises administering a cell-based anti-tumor vaccine. In one aspect, the method further comprises administering an additional anti-cancer agent. Suitable additional anti-cancer agents are selected from the group consisting of an anti-cancer vaccine, e.g., a cell-based anti-tumor vaccine, immunotherapy, radiation, photodynamic therapy (PDT), regional or local hyperthermia therapy, and a chemotherapeutic agent. Suitable immunotherapy includes an antibody, a cytokine, a modified cytokine, an immune checkpoint inhibitor, and any derivatives thereof. Optionally, the chemotherapeutic agent is selected from the group consisting of an alkylating agent, an antimetabolite, an anti-microtubule agent, a topoisomerase inhibitor, a cytotoxic antibiotic, and an antibody drug conjugate.

The composition described herein are administered via oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

Preferably, Treg-mediated immune suppression is reduced, e.g., by at least 5%, at least 10%, at least 20%, at least 30%, at least 40%, at least 50%, at least 60%, at least 70%, at least 80%, at least 90%, or 100%. In another case, the cancer comprises a tumor and the tumor is inhibited or reduced in size following administration, e.g., the tumor size is decreased in size by at least 1%, at least 5%, at least 10%, at least 20%, at least 30%, at least 40%, at least 50%, at least 60%, at least 70%, at least 80%, at least 90%, or 100%

Also provided are methods of treating or preventing an autoimmune disorder or an inflammatory disease comprising identifying a subject suffering from or at risk of developing an autoimmune disorder or an inflammatory disease, and administering to the subject an effective amount of a composition comprising an Activin signaling modulator, thereby treating or preventing an autoimmune disorder or an inflammatory disease in the subject. For example, the Activin signaling modulator comprises an Activin agonist. Preferably, immune tolerance is increased. Activin agonists include preparation of the molecule itself (such as recombinant Activin protein) or portions of Activin. Additionally, pharmacological mimics of Activin designed or identified based on their ability to activate signaling downstream of the Activin Receptor molecule are examples of potential agonists of Activin signaling.

Method of increasing immune tolerance in a subject are carried out by administering to the subject an effective amount of a composition comprising an Activin agonist and increasing Treg function, activity, or proliferation, thereby increasing immune tolerance in a subject. Optionally, the agonist is administered prior to, simultaneously with, or subsequent to administering adoptive cell therapy to the subject to treat transplant/graft rejection, graft-versus-host disease, inflammatory diseases (such as inflammatory bowel disease) or autoimmune disease (such as multiple sclerosis, psoriasis).

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

Antibodies and fragments thereof described herein include, but are not limited to, polyclonal, monoclonal, chimeric, dAb (domain antibody), single chain, Fab, Fab' and F(ab')2 fragments, Fv, scFvs. A fragment of an antibody possess the immunological activity of its respective antibody. In some embodiments, a fragment of an antibody contains 1500 or less, 1250 of less, 1000 or less, 900 or less, 800 or less, 700 or less, 600 or less, 500 or less, 400 or less, 300 or less, 200 or less amino acids. For example, a protein or peptide inhibitor contains 1500 or less, 1250 of less, 1000 or less, 900 or less, 800 or less, 700 or less, 600 or less, 500 or less, 400 or less, 300 or less, 200 or less, 100 or less, 80 or less, 70 or less, 60 or less, 50 or less, 40 or less, 30 or less, 25 or less, 20 or less, 10 or less amino acids. For example, a nucleic acid inhibitor of the invention contains 400 or less, 300 or less, 200 or less, 150 or less, 100 or less, 90 or less, 80 or less, 70 or less, 60 or less, 50 or less, 40 or less, 35 or less, 30 or less, 28 or less, 26 or less, 24 or less, 22 or less, 20 or less, 18 or less, 16 or less, 14 or less, 12 or less, 10 or less nucleotides.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The term "antagonist antibody" is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

By "agent" is meant any small compound, antibody, nucleic acid molecule, or polypeptide, or fragments thereof.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

By "alteration" is meant a change (increase or decrease) in the expression levels or activity of a gene or polypeptide as detected by standard art known methods such as those described herein. As used herein, an alteration includes at least a 1% change in expression levels, e.g., at least a 2%, 3%, 4%, 5%, 6%, 7%, 8%, 9%, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease. Ameliorate refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between any two of these values. Such improvement or change may be observed in treated subjects as compared to subjects not treated with an agent, where the untreated subjects have, or are subject to developing, the same or similar injury/condition, disease, or symptom. Amelioration of an injury/condition, disease, symptom or assay parameter may be determined subjectively or objectively, e.g., via self-assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s), by detection of disorders in a subject, and/or by modalities such as, but not limited to photographs, video, digital imaging and physiological function tests. Amelioration may be transient, prolonged or permanent, or it may be variable at relevant times during or after an agent is administered to a subject or is used in an assay or other method described herein or a cited reference, e.g., within timeframes described infra, or about 12 hours to 24 or 48 hours after the administration or use of an agent to about 3, 4, 5, 6, 7, 8, 9, 10, 11, 12, 13, 14, 21, 28 days, or 1, 3, 6, 9 months or more after a subject(s) has received such treatment.

By "binding to" a molecule is meant having a physicochemical affinity for that molecule.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

By "control" or "reference" is meant a standard of comparison. As used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

"Detect" refers to identifying the presence, absence or amount of the analyte to be detected.

As used herein, the term "diagnosing" refers to classifying pathology or a symptom, determining a severity of the pathology (e.g., grade or stage), monitoring pathology progression, forecasting an outcome of pathology, and/or determining prospects of recovery.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease, e.g., cancer, relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

By "marker" is meant any protein or polynucleotide having an alteration in expression level or activity that is associated with a disease or disorder.

By "modulate" is meant alter (increase or decrease). Such alterations are detected by standard art known methods such as those described herein. The modulation of, e.g., a symptom, level or biological activity of a molecule, refers, for example, to the symptom or activity that is detectably increased or decreased. Such increase or decrease may be observed in treated subjects as compared to subjects not treated with an agent, where the untreated subjects have, or are subject to developing, the same or similar disease, condition, symptom. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self-assessment, by a clinician's assessment or by conducting an appropriate assay or measurement, including, e.g., quality of life assessments, suitable assays for the level or activity of molecules, cells or cell migration within a subject and/or by modalities such as, but not limited to photographs, video, digital imaging and physiological function tests. Modulation may be transient, prolonged or permanent or it may be variable at relevant times during or after an agent is administered to a subject or is used in an assay or other method described herein or a cited reference, e.g., within times described infra, or about 12 hours to 24 or 48 hours after the administration or use of an agent to about 3, 4, 5, 6, 7, 8, 9, 10, 11, 12, 13, 14, 21, 28 days, or 1, 3, 6, 9 months or more after a subject(s) has received such treatment.

By "cancer" (also called neoplasia, hyperproliferative disorder, dysplasia, malignant tumor, and/or malignant neoplasia) is meant a group of diseases involving abnormal cell growth with the potential to invade or spread to other parts of the body. Not all tumors are cancerous; benign tumors do not spread to other parts of the body. There are over 100 different known cancers that affect humans.

The term "autoimmunity" refers to the series of immune responses of an organism against its own cells and tissues. "Autoimmune disease" is any disease caused by an aberrant immune response. Examples of autoimmune disease include but are not limited to: Addison's Disease, ankylosing spondylitis, Celiac disease, Churg-Strauss Syndrome, dermatomyositis (DM), diabetes mellitus type 1, Graves' disease, Hashimoto's thyroiditis, idiopathic thrombocytopenic purpura, polymyositis (PM), rheumatoid arthritis (RA), sarcoidosis, Sjögren's syndrome, and systemic lupus erythematosus (SLE).

The term "inflammation" refers to the series of biological responses to harmful stimuli by an organism's tissues, such as irritants, damaged cells, or pathogens. Inflammation is a protective response that involves immune system cells as well as molecular mediators (for example, cytokines) and the circulatory system (blood vessels). The main role of inflammation is to eliminate the initial cause of cell injury, clear out necrotic cells and damaged tissues, and initiate repair of tissues.

The term, "normal amount" refers to a normal amount of a complex in an individual known not to be diagnosed with a disease or disorder. The amount of the molecule can be measured in a test sample and compared to the "normal control level," utilizing techniques such as reference limits, discrimination limits, or risk defining thresholds to define cutoff points and abnormal values (e.g., for pancreatitis). The "normal control level" means the level of one or more proteins (or nucleic acids) or combined protein indices (or combined nucleic acid indices) typically found in a subject known not to be suffering from prostate cancer. Such normal control levels and cutoff points may vary based on whether a molecule is used alone or in a formula combining other proteins into an index. Alternatively, the normal control level can be a database of protein patterns from previously tested subjects who did not convert to a disease or disorder over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease in question or is not at risk for the disease.

Relative to a control level, the level that is determined may be an increased level. As used herein, the term "increased" with respect to level (e.g., expression level, biological activity level, etc.) refers to any % increase above a control level. The increased level may be at least or about a 1% increase, at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, or at least or about a 95% increase, relative to a control level.

Relative to a control level, the level that is determined may be a decreased level. As used herein, the term "decreased" with respect to level (e.g., expression level, biological activity level, etc.) refers to any % decrease below a control level. The decreased level may be at least or about a 1% decrease, at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, or at least or about a 95% decrease, relative to a control level.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body.

Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

A "purified" or "biologically pure" nucleic acid or protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 1%, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

By "reference" is meant a standard or control condition.

A "reference sequence" is a defined sequence used as a basis for sequence comparison or a gene expression comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 40 nucleotides, preferably at least about 60 nucleotides, more preferably at least about 75 nucleotides, and even more preferably about 100 nucleotides or about 300 or about 500 nucleotides or any integer thereabout or there between.

As used herein, "obtaining" as in "obtaining an agent" includes synthesizing, purchasing, or otherwise acquiring the agent.

The term "subject" as used herein includes all members of the animal kingdom prone to suffering from the indicated disorder. In some aspects, the subject is a mammal, including, but not limited to, a human or non-human mammal, such as a bovine, equine, canine, ovine, or feline. The subject is preferably a mammal in need of treatment, e.g., a subject that has been diagnosed with a disease or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The term "sample" as used herein refers to a biological sample obtained for the purpose of evaluation in vitro. With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis). Preferred samples are whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

By "specifically binds" is meant a compound or antibody that recognizes and binds a polypeptide of the invention, but which does not substantially recognize and bind other molecules in a sample, for example, a biological sample, which naturally includes a polypeptide of the invention.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with increased immune suppression is within the ability of those in the art. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The terms "treat," treating," "treatment," and the like as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

The terms "prevent", "preventing", "prevention", "prophylactic treatment" and the like refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in arresting cell cycle in rapidly dividing cells, e.g., cancer cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

A "therapeutically effective amount" is an amount sufficient to effect beneficial or desired results, including clinical results. An effective amount can be administered in one or more administrations.

Any compositions or methods provided herein can be combined with one or more of any of the other compositions and methods provided herein.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 2A shows freshly isolated CD4+CD25− T cells were cultured with plate bound anti-CD3 (2 µg/ml) and solute anti-CD28 (2 µg/ml) for 24 hrs, followed by treatment with different concentrations of Activin A and TGF-β as indicated for additional 12 hours. Cells were harvested and subjected to SDS-PAGE and Western blot with the indicated antibodies. FIG. 2B shows that iTreg differentiation of WT and Foxp3Cre-driven YAP knockout mice (Foxp3Cre+/YAPfl/fl) in the presence of IL-2 and varying concentrations of TGF-β was assessed by intracellular staining for Foxp3 and flow cytometry analysis.

FIG. 5A shows that genes (n=311) significantly changed by YAP knockout in naïve T, unstimulated Treg, or stimulated Treg cells were used to make the heatmap. Clustering was done with the complete linkage and euclidean distance. The color representation from green to red denotes log2-transformed FPKM from −2 to 2. FIG. 5B depicts the qRTPCR measurement of Activin A receptor (ACVR1c) expression in T cell subsets. Total mRNA was isolated from naïve CD4+ T cells, Tregs differentiating in vitro ("iTregs"), and isolated CD25+/CD4+ Tregs (natural, "nTregs"). From these samples, cDNA was generated and RTPCR was carried out.

The transduced Tregs were co-cultured with CFSE-stained CD45.1+naïve CD4+T cells (responders) at the indicated ratio and antigen presenting cells (T cell depleted splenocytes). After 5 days of activation, responder cell proliferation was assessed by flow cytometry. Shown are responder cell gated (CD45.1+/CD4+) events.

Figure 7:
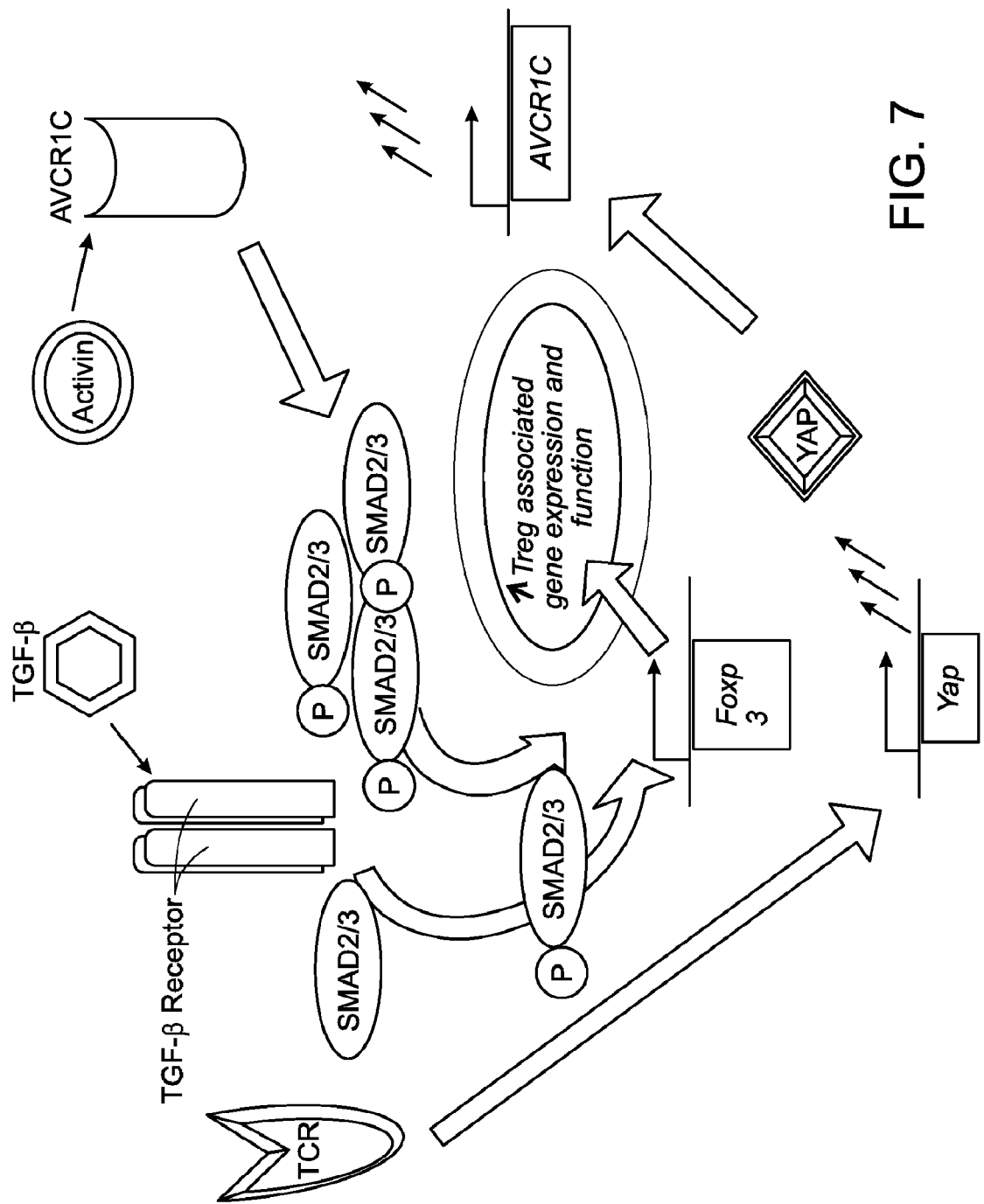

FIG. 7 is a diagram depicting a model for YAP-mediated TGF-β/SMAD signaling enhancement. YAP is up-regulated during TGF-β-driven differentiation of Tregs. YAP drives expression of the Activin Receptor, AVCR1C, ligation of which enhances SMAD activity, and promotes continued Foxp3 expression and Treg function.

Figure 8A:
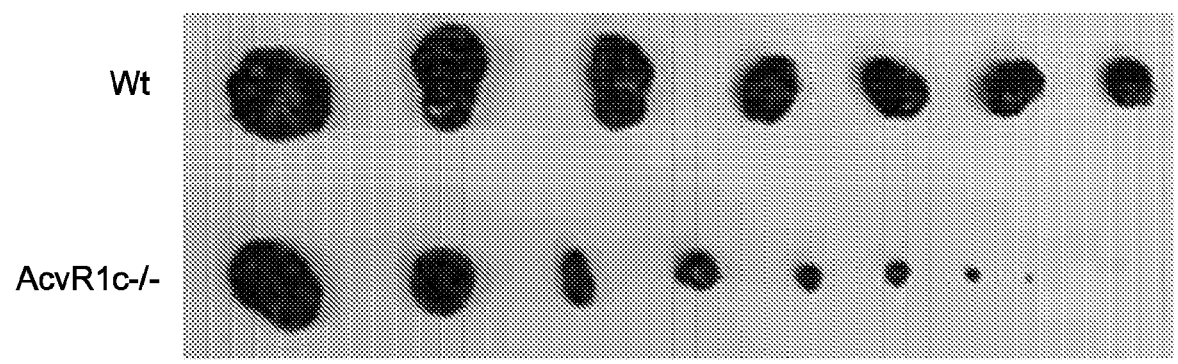
Figure 8B:
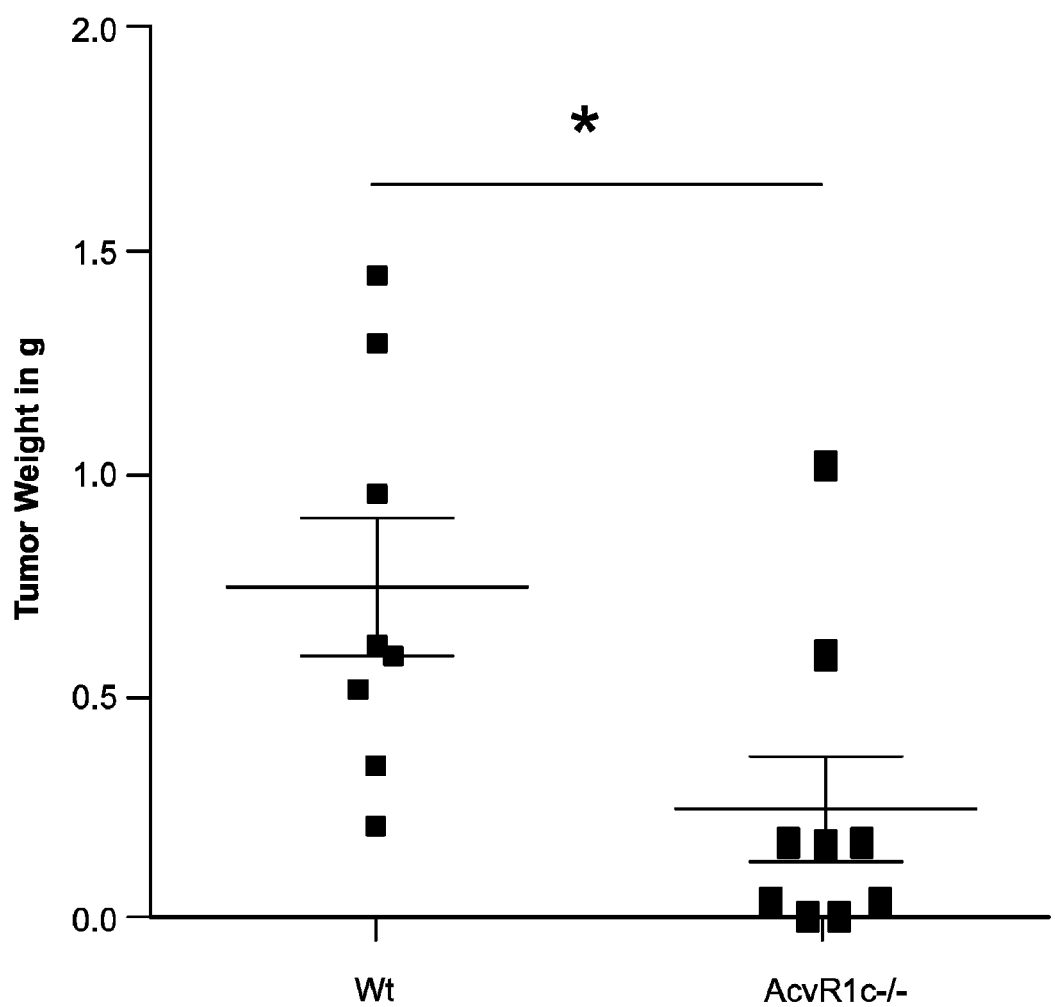
Figure 8C:
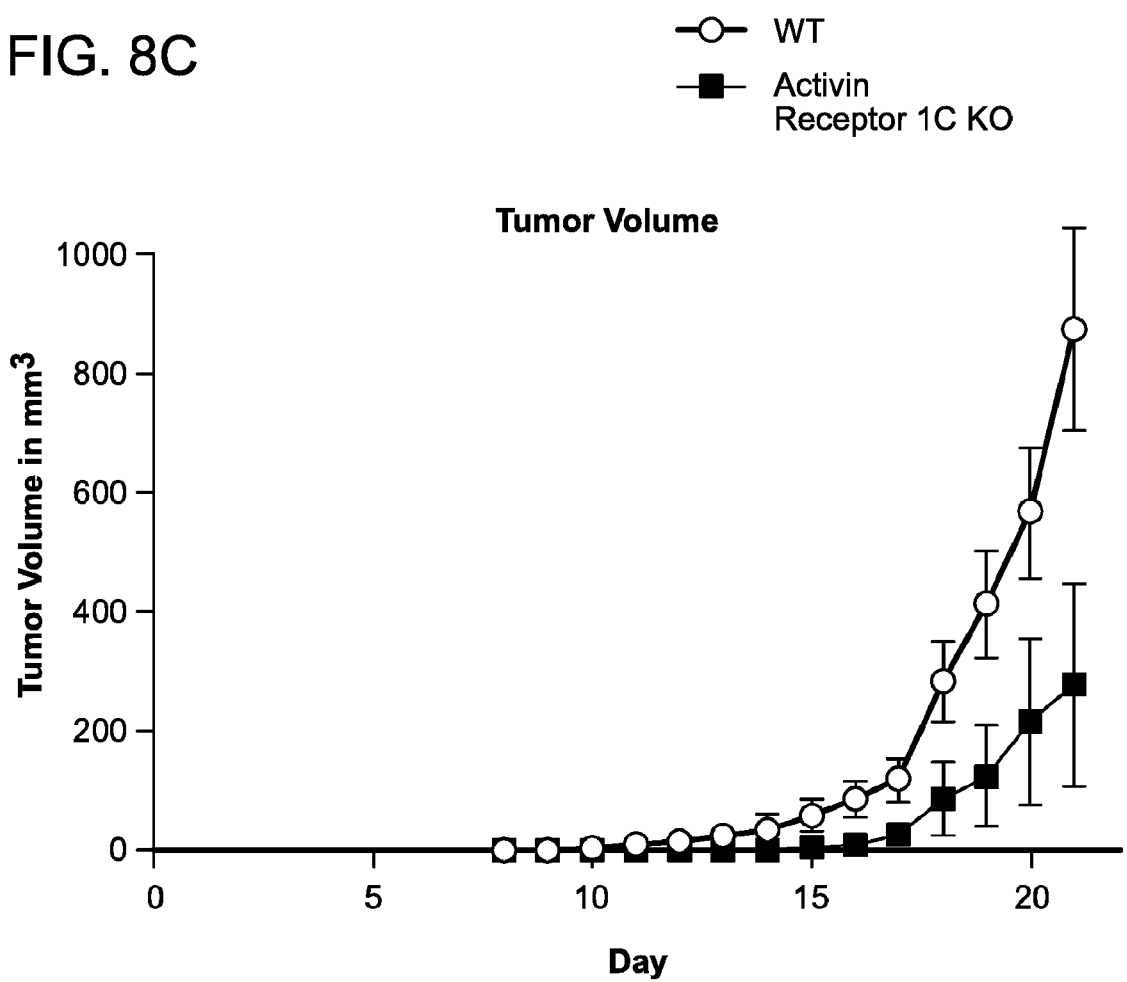

FIG. 8A-FIG. 8C is a photograph, a dot plot, and a line graph showing that mice lacking Activin Receptor 1C grow smaller tumors. FIG. 8A shows a photograph of excised tumors on day 22. FIG. 8B shows the mean and standard error of the mean (SEM) of tumor weights on day 22. FIG. 8C shows mean and SEM tumor volume for each day.

DETAILED DESCRIPTION OF THE INVENTION

The present invention is based, at least in part, upon the development of methods of treating cancer by targeting Activin signaling to modulate Treg cell function, activity, or proliferation. As described in detail below, antibody-mediated ablation of Activin signaling suppressed the growth of tumors. Additionally, as described herein, inhibition of Activin signaling improved the effectiveness of cell-based anti-tumor vaccines when both are used in combination.

Regulatory T (Treg) cells are important for maintaining immune homeostasis, but, in the tumor microenvironment, these immunosuppressive cells hinder effective anti-tumor immune responses and immunotherapies. Foxp3 is a canonical transcription factor expressed in Tregs and is required for their function. However, prior to the invention described herein, the pathways and micro-environmental cues that affect Foxp3 expression and Treg function were not completely understood. As described herein, Treg cells readily express the molecule Activin, which significantly contributes to the development and suppressive function of these cells. Furthermore, as detailed herein, RNAseq and qRTPCR analysis showed that Activin Receptor 1c (ACVR1C or ALK7) was down-regulated in Tregs lacking YAP. Additionally, the Activin Receptor (ACVR1) is highly up-regulated in developing and activated Treg cells. As described in detail below, Activin treatment of T cells triggers activation of the SMAD signaling cascade known to be important for signaling induced by TGFI3, and Activin can synergize with this notoriously anti-inflammatory cytokine to augment SMAD activation and promote the generation of Tregs. Exposure to Activin resulted in amplification of TGFI3 signaling and Foxp3 induction in wt but not YAP−/− Treg. Forced expression of ACVR1c by YAP−/− Tregs could rescue suppressive activity. As described in the Examples below, antibody-mediated ablation of Activin signaling suppressed the growth of B16-melanoma tumors in mice, suggesting that Activin contributes to Treg-enforced immune tolerance in the tumor setting. Furthermore, as detailed below, Activin blockade slowed tumor growth and improved the effectiveness of an anti-tumor vaccine in an aggressive, poorly immunogenic mouse model of melanoma. Thus, the results presented herein identify a previously unrecognized, feed-forward regulatory loop for amplifying TGFβ/SMAD pathway signaling that lends itself to therapeutic disruption. Furthermore, as described herein, such therapeutic disruption of the Activin/ACVR1C axis yields superior anti-tumor immunity. This discovery informs a new therapeutic approach to cancer that combines the targeting of Activin-Activin Receptor-induced signaling with other immuno-therapies that enhance immune responses such as checkpoint inhibition and vaccination.

Regulatory T cells (Tregs)

The regulatory T cells (Tregs), are a subpopulation of T cells which modulate the immune system, maintain tolerance to self-antigens, and abrogate autoimmune disease. These cells generally suppress or downregulate induction and proliferation of effector T cells.

Additional regulatory T cells known as Treg17 cells have recently been identified. Mouse models have suggested that modulation of Tregs can treat autoimmune disease and cancer, and facilitate organ transplantation.

T regulatory cells are a component of the immune system that suppress immune responses of other cells. This is an important check built into the immune system to prevent excessive reactions. Regulatory T cells come in many forms with the most well-understood being those that express CD4, CD25, and Foxp3 (CD4+CD25+ regulatory T cells). These "Tregs" are different from helper T cells. Another regulatory T cell subset is Treg17 cells. Regulatory T cells are involved in shutting down immune responses after they have successfully eliminated invading organisms, and also in preventing autoimmunity.

CD4+ Foxp3+ regulatory T cells have been called "naturally-occurring" regulatory T cells to distinguish them from "suppressor" T cell populations that are generated in vitro. Additional regulatory T cell populations include Tr1, Th3, CD8+CD28−, and Qa-1 restricted T cells. The contribution of these populations to self-tolerance and immune homeostasis is less well defined. FOXP3 can be used as a good marker for mouse CD4+CD25+ T cells, although recent studies have also shown evidence for FOXP3 expression in CD4+CD25− T cells. In humans, FoxP3 is also expressed by recently activated conventional T-cells and thus does not specifically identify human T-reg.

All T cells come from progenitor cells from the bone marrow, which become committed to their lineage in the thymus. All T cells begin as CD4−CD8−TCR− cells at the DN (double-negative) stage, where an individual cell will rearrange its T cell receptor genes to form a unique, functional molecule, which they, in turn, test against cells in the thymic cortex for a minimal level of interaction with self-MHC. If they receive these signals, they proliferate and express both CD4 and CD8, becoming double-positive cells. The selection of Tregs occurs on radio-resistant hemopoietically-derived MHC class II-expressing cells in the medulla or Hassal's corpuscles in the thymus. At the DP (double-positive) stage, they are selected by their interaction with the cells within the thymus, begin the transcription of Foxp3, and become Treg cells, although they may not begin to express Foxp3 until the single-positive stage, at which point they are functional Tregs. Tregs do not have the limited TCR expression of NKT or γδ T cells; Tregs have a larger TCR diversity than effector T cells, biased towards self-peptides.

The process of Treg selection is determined by the affinity of interaction with the self-peptide MHC complex. T cell that receives very strong signals will undergo apoptotic death; a cell that receives a weak signal will survive and be selected to become an effector cell. If a T cell receives an intermediate signal, then it will become a regulatory cell. Due to the stochastic nature of the process of T cell activation, all T cell populations with a given TCR will end up with a mixture of Teff and Treg—the relative proportions determined by the affinities of the T cell for the self-peptide-MHC. Even in mouse models with TCR-transgenic cells selected on specific-antigen-secreting stroma, deletion or conversion is not complete.

Foxp3+ Treg generation in the thymus is delayed by several days compared to Teff cells and does not reach adult levels in either the thymus or periphery until around three weeks post-partum. Treg cells require CD28 co-stimulation and B7.2 expression is largely restricted to the medulla, the development of which seems to parallel the development of Foxp3+ cells. It has been suggested that the two are linked, but no definitive link between the processes has yet been shown. TGF-β is not required for Treg functionality, in the thymus, as thymic Treg from TGF-β insensitive TGFβRII-DN mice are functional.

The immune system must be able to discriminate between self and non-self. When self/non-self discrimination fails, the immune system destroys cells and tissues of the body and as a result causes autoimmune diseases. Regulatory T cells actively suppress activation of the immune system and prevent pathological self-reactivity, i.e. autoimmune disease. The critical role regulatory T cells play within the immune system is evidenced by the severe autoimmune syndrome that results from a genetic deficiency in regulatory T cells (IPEX syndrome).

The molecular mechanism by which regulatory T cells exert their suppressor/regulatory activity has not been definitively characterized and is the subject of intense research. In vitro experiments have given mixed results regarding the requirement of cell-to-cell contact with the cell being suppressed. The immunosuppressive cytokines TGF-beta and Interleukin 10 (IL-10) have also been implicated in regulatory T cell function.

Induced Regulatory T (iTreg) cells (CD4+ CD25+ Foxp3+) are suppressive cells involved in tolerance. iTreg cells have been shown to suppress T cell proliferation and experimental autoimmune diseases. These cells include Treg17 cells. Induced Treg cells develop from mature CD4+ conventional T cells outside of the thymus: a defining distinction between natural regulatory T (nTreg) cells and iTreg cells. Though iTreg and nTreg cells share a similar function iTreg cells have recently been shown to be "an essential non-redundant regulatory subset that supplements nTreg cells, in part by expanding TCR diversity within regulatory responses". Acute depletion of the iTreg cell pool in mouse models has resulted in inflammation and weight loss. The contribution of nTreg cells versus iTreg cells in maintaining tolerance is unknown, but both are important. Epigenetic differences have been observed between nTreg and iTreg cells, with the former having more stable Foxp3 expression and wider demethylation.

CD4+ Regulatory T cells are often associated with solid tumors in both humans and murine models. Increased numbers of regulatory T cells in breast, colorectal and ovarian cancers is associated with a poorer prognosis. CD70+ non-Hodgkin lymphoma B cells induce Foxp3 expression and regulatory function in intratumoral CD4+CD25− T cells. A recent study shows that cerebral ischemia can increase bone marrow CD4(+)CD25(+)FoxP3(+) regulatory T cells via signals from the sympathetic nervous system.

Similar to other T cells, regulatory T cells develop in the thymus. The latest research suggests that regulatory T cells are defined by expression of the forkhead family transcription factor FOXP3 (forkhead box p3). Expression of FOXP3 is required for regulatory T cell development and appears to control a genetic program specifying this cell's fate. The large majority of Foxp3-expressing regulatory T cells are found within the major histocompatibility complex (MHC) class II restricted CD4-expressing (CD4+) population and express high levels of the interleukin-2 receptor alpha chain (CD25). In addition to the Foxp3-expressing CD4+ CD25+, there also appears to be a minor population of MHC class I restricted CD8+ Foxp3-expressing regulatory T cells. These Foxp3-expressing CD8+ T cells do not appear to be functional in healthy individuals but are induced in autoimmune disease states by T cell receptor stimulation to suppress IL-17-mediated immune responses. Unlike conventional T cells, regulatory T cells do not produce IL-2 and are therefore anergic at baseline.

A number of different methods are employed to identify and monitor Treg cells. Originally, high expression of CD25 and CD4 surface markers was used (CD4+CD25+ cells). This is problematic as CD25 is also expressed on non-regulatory T cells in the setting of immune activation such as during an immune response to a pathogen. As defined by CD4 and CD25 expression, regulatory T cells comprise about 5-10% of the mature CD4+ T cell subpopulation in mice and humans, while about 1-2% of Treg can be measured in whole blood. The additional measurement of cellular expression of Foxp3 protein allowed a more specific analysis of Treg cells (CD4+CD25+ Foxp3+ cells). However, Foxp3 is also transiently expressed in activated human effector T cells, thus complicating a correct Treg analysis using CD4, CD25 and Foxp3 as markers in humans. Therefore, some use another marker, the absence or low-level expression of the surface protein CD127 in combination with the presence of CD4 and CD25. Several additional markers have been described, e.g., high levels of CTLA-4 (cytotoxic T-lymphocyte associated molecule-4) and GITR (glucocorticoid-induced TNF receptor) are also expressed on regulatory T cells, however the functional significance of this expression remains to be defined. There is a great interest in identifying cell surface markers that are uniquely and specifically expressed on all Foxp3-expressing regulatory T cells. However, to date no such molecule has been identified.

Genetic mutations in the gene encoding Foxp3 have been identified in both humans and mice based on the heritable disease caused by these mutations. This disease provides the most striking evidence that regulatory T cells play a critical role in maintaining normal immune system function. Humans with mutations in Foxp3 suffer from a severe and rapidly fatal autoimmune disorder known as Immune dysregulation, Polyendocrinopathy, Enteropathy X-linked (IPEX) syndrome.

The IPEX syndrome is characterized by the development of overwhelming systemic autoimmunity in the first year of life, resulting in the commonly observed triad of watery diarrhea, eczematous dermatitis, and endocrinopathy seen most commonly as insulin-dependent diabetes mellitus. Most individuals have other autoimmune phenomena including Coombs-positive hemolytic anemia, autoimmune thrombocytopeni a, autoimmune neutropenia, and tubular nephropathy. The majority of affected males die within the first year of life of either metabolic derangements or sepsis. An analogous disease is also observed in a spontaneous Foxp3-mutant mouse known as "scurfy".

Regulatory T cells (Tregs) play critical roles in promoting immunological self-tolerance and immune homeostasis by suppressing aberrant or excessive immune responses that could give rise to autoimmune diseases (Sakaguchi, S., et al., Cell, 2008. 133:775-87). However, they also represent a major barrier to effective anti-tumor immunity and sterilizing immunity to chronic infections (Whiteside, T. L., Semin Cancer Biol, 2012. 22:327-34). The signature forkhead family transcription factor, Foxp3, anchors the gene expression profile that is responsible for the characteristic suppressive function of Tregs. Clearly demonstrating its importance, mutations in the gene encoding Foxp3 lead to autoimmune disorders in Scurfy mice and in human IPEX patients alike (Bennett, C. L., et al., Nat Genet, 2001. 27:20-1; Brunkow, M. E., et al., Nat Genet, 2001. 27:68-73).

In general terms, Tregs have been classified into two different subtypes determined by the tissues where they develop. Thymus-derived or "natural" Treg (tTreg) constitute the majority of circulating Foxp3+ Tregs and are crucial for preventing autoimmunity. Tregs induced in peripheral tissues (pTregs) or ex vivo (iTreg) arise from naïve T cells in the periphery that acquire Foxp3 expression and suppressive function. This occurs through the activation of the TGF-β/IL-2 signaling pathways (Josefowicz, S. Z., et al., Annu Rev Immunol, 2012. 30:531-64). TGF-I3 is a potent inducer of Foxp3 expression in vitro and in vivo and members of the SMAD family of signaling molecules serve as critical facilitators and regulators of TGF-β-initiated signaling events and downstream gene activation (Zheng, Y., et al., Nature, 2010. 463:808-12).

TGF-β signaling has also been reported to be critical for maintaining Foxp3 expression and Treg function (Marie, J. C., et al., J Exp Med, 2005. 201:1061-7; Liu, Y., et al., Nat Immunol, 2008. 9:632-40). Likewise SMAD2 and SMAD3 are also apparently needed for optimal stability of Tregs (Takimoto, T., et al., J Immunol, 2010. 185:842-55). Mechanisms for the augmentation or amplification of TGF-13/SMAD signaling in Tregs can stabilize or enhance the suppressive function of these cells (Wu C., et al., Immunity, 2014. 41:270-82) in a variety of microenvironmental niches. In addition to contributing to Treg development and function, this notoriously anti-inflammatory cytokine is known to have direct suppressive effects on other immune cells.

Foxp3

FOXP3 (forkhead box P3), also known as scurfin, is a protein involved in immune system responses. A member of the FOX protein family, FOXP3 appears to function as a master regulator (transcription factor) in the development and function of regulatory T cells. Regulatory T cells generally turn the immune response down. In cancer, an excess of regulatory T cell activity can prevent the immune system from destroying cancer cells. In autoimmune disease, a deficiency of regulatory T cell activity can allow other autoimmune cells to attack the body's own tissues.

While the precise control mechanism has not yet been established, FOX proteins belong to the forkhead/winged-helix family of transcriptional regulators and are presumed to exert control via similar DNA binding interactions during transcription. In regulatory T cell model systems, the FOXP3 transcription factor occupies the promoters for genes involved in regulatory T-cell function, and may repress transcription of key genes following stimulation of T cell receptors.

The human FOXP3 genes contain 11 coding exons. Exon-intron boundaries are identical across the coding regions of the mouse and human genes. By genomic sequence analysis, the FOXP3 gene maps to the p arm of the X chromosome (specifically, Xp11.23).

The discovery of Foxp3 as a specific marker of natural T regulatory cells (nTregs, a lineage of T cells) and adaptive/induced T regulatory cells (a/iTregs) gave a molecular anchor to the population of regulatory T cells (Tregs), previously identified by non-specific markers such as CD25 or CD45RB.

In animal studies, Tregs that express Foxp3 are critical in the transfer of immune tolerance, especially self-tolerance. The induction or administration of Foxp3 positive T cells has, in animal studies, led to marked reductions in (autoimmune) disease severity in models of diabetes, multiple sclerosis, asthma, inflammatory bowel disease, thyroiditis and renal disease. Human trials have produced weaker results.

T helper 17 (Th17) cells are proinflammatory and are produced under similar environments as a/iTregs. Th17 cells are produced under the influence of TGF-β and IL-6 (or IL-21), whereas a/iTregs are produced under the influence of solely TGF-β, so the difference between a proinflammatory and a pro-regulatory scenario is the presence of a single interleukin. IL-6 or IL-21 is being debated by immunology laboratories as the definitive signaling molecule. Murine studies point to IL-6 whereas human studies have shown IL-21.

In human disease, alterations in numbers of regulatory T cells—and in particular those that express Foxp3—are found in a number of disease states. For example, patients with tumors have a local relative excess of Foxp3 positive T cells which inhibits the body's ability to suppress the formation of cancerous cells. Conversely, patients with an autoimmune disease such as systemic lupus erythematosus (SLE) have a relative dysfunction of Foxp3 positive cells. The Foxp3 gene is also mutated in the X-linked IPEX syndrome (Immuno-dysregulation, Polyendocrinopathy, and Enteropathy, X-linked). These mutations were in the forkhead domain of FOXP3, indicating that the mutations may disrupt critical DNA interactions.

In mice, a Foxp3 mutation (a frameshift mutation that result in protein lacking the forkhead domain) is responsible for "Scurfy", an X-linked recessive mouse mutant that results in lethality in hemizygous males 16 to 25 days after birth. These mice have overproliferation of CD4+ T-lymphocytes, extensive multiorgan infiltration, and elevation of numerous cytokines. This phenotype is similar to those that lack expression of CTLA-4, TGF-β, human disease IPEX, or deletion of the Foxp3 gene in mice ("scurfy mice"). The pathology observed in scurfy mice seems to result from an inability to properly regulate CD4+ T-cell activity. In mice overexpressing the Foxp3 gene, fewer T cells are observed. The remaining T cells have poor proliferative and cytolytic responses and poor interleukin-2 production, although thymic development appears normal. Histologic analysis indicates that peripheral lymphoid organs, particularly lymph nodes, lack the proper number of cells.

In addition to FoxP3's role in regulatory T cell differentiation, multiple lines of evidence have indicated that FoxP3 play important roles in cancer development. Down-regulation of FoxP3 expression has been reported in tumor specimens derived from breast, prostate, and ovarian cancer patients, indicating that FoxP3 is a potential tumor suppressor gene. Expression of FoxP3 was also detected in tumor specimens derived from additional cancer types, including pancreatic, melanoma, liver, bladder, thyroid, cervical cancers. However, in these reports, no corresponding normal tissues was analyzed, therefore it remained unclear whether FoxP3 is a pro- or anti-tumorigenic molecule in these tumors.

Two lines of functional evidence strongly supported that FoxP3 serves as tumor suppressive transcription factor in cancer development. First, FoxP3 represses expression of HER2, Skp2, SATB1 and MYC oncogenes and induces expression of tumor suppressor genes P21 and LATS2 in breast and prostate cancer cells. Second, over-expression of FoxP3 in melanoma, glioma, breast, prostate and ovarian cancer cell lines induces profound growth inhibitory effects in vitro and in vivo. However, this hypothesis need to be further investigated in future studies.

Activin

Activin (or Activin A) is a dimeric member of the TGF-β Superfamily well known for its ability to promote Follicle Stimulating Hormone activity and a variety of cellular processes (Chen, Y. G., et al., Exp Biol Med (Maywood), 2006. 231:534-44). It has also been studied for its role in wound repair and fibrosis (Sulyok, S., et al., Mol Cell Endocrinol, 2004. 225:127-32), and it has also been linked to cancer metastasis (Wamsley, J. J., et al., Cancer Res, 2015. 75:426-35). Activin has been reported to augment SMAD signaling in non-immune cells (Schmierer, B., et al., J Biol Chem, 2003. 278:21197-203). Additionally, Activin levels are markedly elevated in the serum during pregnancy, a state known to witness the bolstering of induced Tregs frequencies, which contribute to maternal tolerance of the developing fetus (Teles, A., et al., Am J Clin Exp Immunol, 2013. 2:222-33).

In light of its expression in decidedly tolerogenic microenvironments and physiological states, coupled with its link to TGF-β signaling, the Activin pathway is important in YAP-mediated Treg function. As described herein, whole transcriptome analysis of genes differentially expressed by Tregs with and without YAP revealed that the receptor for a molecule known as Activin (ACVR1C/ALK7) falls under the control of this transcriptional coactivator. Indeed, there is a role for Activin in amplifying TGF-β/SMAD signaling and the promotion of Treg differentiation and in aiding the progression of tumors.

As described herein, Activin is constitutively expressed by Tregs and the Activin receptor (ACVR1C) was also found to be highly expressed by Tregs, but specifically so on activated and differentiating Tregs. Furthermore, exposure of T cells to Activin led to enhanced SMAD-signaling and bolstered Foxp3 expression and commitment to the Treg lineage. As described in detail below, antagonizing Activin activity by monoclonal antibody-mediated blockade dramatically slowed the growth of tumors in a highly aggressive mouse model of melanoma. Finally, as described herein, this treatment also enhanced the anti-tumor efficacy of an immunotherapeutic anti-tumor vaccine.

Activin enhances FSH biosynthesis and secretion, and participates in the regulation of the menstrual cycle. Many other functions have been found to be exerted by activin, including roles in cell proliferation, differentiation, apoptosis, metabolism, homeostasis, immune response, wound repair, and endocrine function.

Activin is a dimer composed of two identical or very similar beta subunits. Activin and a number of other structurally related proteins such as anti-Müllerian hormone, bone morphogenetic protein, and growth differentiation factor belong to the TGF-β protein superfamily The activin protein complex is dimeric in structure, and, the two monomers are linked to one another by a single disulfide bond. In addition, the complex is derived from the same family of related genes and proteins. The alpha and beta subunits share approximately 25% sequence similarity, whereas the similarity between beta subunits is approximately 65%. In mammals, four beta subunits have been described, called activin βA, activin βB, activin βC and activin βE. A fifth subunit, activin βD, has been described in Xenopus laevis. Two activin βA subunits give rise to activin A, one βA, and one βB subunit gives rise to activin AB, and so on. Various, but not all theoretically possible, heterodimers have been described. The subunits are linked by a single covalent disulfide bond. The βC subunit is able to form activin heterodimers with βA or βB subunits Activin is produced in the gonads, pituitary gland, placenta, and other organs. In the ovarian follicle, activin increases FSH binding and FSH-induced aromatization. It participates in androgen synthesis enhancing LH action in the ovary and testis. In the male, activin enhances spermatogenesis. Activin is strongly expressed in wounded skin, and overexpression of activin in epidermis of transgenic mice improves wound healing and enhances scar formation. Its action in wound repair and skin morphogenesis is through stimulation of keratinocytes and stromal cells in a dose-dependent manner Activin also regulates the morphogenesis of branching organs such as the prostate, lung, and especially kidney. Activin A increased the expression level of type-I collagen suggesting that activin A acts as a potent activator of fibroblasts. Lack of Activin during development results in neural developmental defects.

As with other members of the superfamily, Activins interact with two types of cell surface transmembrane receptors (Types I and II) which have intrinsic serine/threonine kinase activities in their cytoplasmic domains: Activin type 1 receptors: ACVR1, ACVR1B, ACVR1C and Activin type 2 receptors: ACVR2A, ACVR2B. Activin binds to the Type II receptor and initiates a cascade reaction that leads to the recruitment, phosphorylation, and activation of Type 1 activin receptor. This then interacts with and then phosphorylates SMAD2 and SMAD3, two of the cytoplasmic SMAD proteins. Smad3 then translocates to the nucleus and interacts with SMAD4 through multimerization, resulting in their modulation as transcription factor complexes responsible for the expression of a large variety of genes.

A mutation in the gene for the Activin receptor ACVR1 results in fibrodysplasia ossificans progressiva, a fatal disease that causes muscle and soft tissue to gradually be replaced by bone tissue. This condition is characterized by the formation of an extra skeleton that produces immobilization and eventually death by suffocation. The mutation in ACVR1 causes activin A, which normally acts as an antagonist of the receptor and blocks osteogenesis (bone growth), to behave as an agonist of the receptor and to induce hyperactive bone growth. Mutations in the ACVR1 gene have also been linked to cancer, especially diffuse intrinsic pontine glioma (DIPG).

The Role of Activin Signaling in Tregs to Treat Cancer

Tregs are indispensable for restraining potentially lethal self-directed (autoimmune) responses or over-exuberant ones mounted against normally harmless commensal microbes (IBD) (Sakaguchi, S., et al., Cell, 2008. 133:775-87). However, in cancer patients, Tregs can be greatly enriched within tumors as well as systemically throughout the patient (Miller, A. M., et al., J Immunol, 2006. 177: 7398-405). The suppressive function of these cells in this setting dampens the effectiveness of tumor-directed immunity and is a major obstacle for developing effective anti-cancer immunotherapies (Klages, K., et al., Cancer Res, 2010. 70:7788-99). Prior to the invention described herein, the grasp of the precise mechanisms by which Tregs function and how these important cells interface with diverse macroenvironmental cues was incomplete.

As described herein, analysis of downstream targets of YAP activity in Treg identified the Activin Receptor (ACVR1C). Furthermore, an important finding is the identification of the Activin-Activin Receptor signaling axis that plays a major role in the augmentation of TGF-β/SMAD signaling and Tregs. This pathway is highly important for the induction of extrathymic Foxp3+ T cells from naïve CD4+ precursors as SMADS bind critical enhancer regions for the Foxp3 gene (Zheng, Y., et al., Nature, 2010. 463: 808-12; Josefowicz, S. Z., et al., Nature, 2012. 482:395-9). It is also important for sustaining Foxp3 expression and suppressive function in Tregs, generally (Tran, D. Q., J Mol Cell Biol, 2012. 4:29-37).

With such reliance on TGF-β and SMAD signaling, it stands to reason that Tregs employ mechanisms to optimize or amplify the downstream signaling events and resultant gene regulation triggered by this pathway. Documented examples of such mechanisms include the enzymatic conversion of latent TGF-βto its active form (Worthington, J. J., et al., Immunity, 2015. 42:903-15) and the triggering of SMAD activation by galectin and CD44 (Wu, C., et al., Immunity, 2014. 41:270-82). The up-regulation of ACVR1C—the receptor for a known enhancer of SMAD signaling (i.e. Activin) in T cells exposed to TGF-β suggests the existence of a positive feedback loop for this decidedly pro-Treg cytokine where Activin/ACVR1C signaling can enhance the downstream signaling events triggered by TGF-β.

This pro-Treg amplification mechanism is susceptible to therapeutic disruption. Based on experiments described below, antibody-mediated Activin blockade is a most effective means for the disruption of Treg- and tumor-abetting TGF-β activation in cancer patients. On the other hand, supplementation of Activin or other therapeutic enhancements of the Activin/ACVR1C axis may have considerable potential as a strategy to correct inadequate immune regulation in settings of autoimmune (MS) or inflammatory disease (IBD).

It is known that serum levels of Activin are elevated during pregnancy (Muttukrishna, S., et al., J Clin Endocrinol Metab, 1996. 81:3328-34)—a state during which there is a need for enhanced Treg induction and function to maintain an atmosphere of immune tolerance to the developing fetus. It is possible that tumors may similarly elevate Activin levels. In which case, serum Activin level may be a biomarker for predicting a state of prevailing immune tolerance, predicting both patient prognosis and responsiveness to cancer vaccines and immunotherapies. Additionally patient Activin levels may be used to justify particular immunotherapeutic treatment options (i.e., Treg and/or TGF-β depletion/inhibition).

For these reasons, and in light of the experiments described below, further study of the Activin/ACVR1C axis in the promotion of immune tolerance is warranted. Such work stands to yield insights into the mechanisms by which Tregs can optimize cues from the microenvironment (such as cytokines like TGF-β to maintain their function. Additionally, the development and vetting of therapeutic antibodies capable of neutralizing Activin or blocking its association with ACVR1C in cancer patients may lead to new and potent immunotherapeutic regiments to unleash anti-tumor immunity from stifling Treg-enforced tolerance.

Described herein is a role for Activin, not only in amplifying of TGF-β/SMAD signaling and the promotion of Treg differentiation, but also in aiding the progression of tumors. Activin is highly expressed and constitutively expressed by Tregs. As described in detail below, the Activin receptor (ACVR1C) was also found to be highly expressed by Tregs, but specifically on activated and differentiating Tregs. Furthermore, exposure of T cells to Activin led to enhanced SMAD-signaling and bolstered Foxp3 expression and commitment to the Treg lineage. Antagonizing Activin activity by monoclonal antibody-mediated blockade dramatically slowed the growth of tumors in a highly aggressive mouse model of melanoma. This experimental treatment also enhanced the anti-tumor efficacy of an immunotherapeutic anti-tumor vaccine.

These findings suggest that Activin plays an important role in the induction and maintenance of Foxp3 expression and Treg-enforced tolerance. Moreover, they clearly identify this factor as a tempting target for therapeutic manipulation.
The Role of Activin Signaling in Tregs to Treat Autoimmunity o Inflammation Due to its role in Treg development, the supplemental administration of Activin and/or Activin analogs may be used to increase immune tolerance. As described herein, stimulating Treg development with Activin or Activin analogs is a novel approach to treating disorders involving immune tolerance, such as autoimmunity or inflammation. In some embodiments, Activin and/or Activin analogs are used to treat autoimmunity or inflammation.

Provided herein are methods for treating cancer or other disorders by targeting the Activin signaling pathway. These methods may include inhibitors, neutralizing antibodies, antagonists, and other strategies to inhibit or regulate Activin signaling Inhibitors of Activin or Activin Receptor expression are intended to undermine Treg development, function and immune tolerance in a cancer setting. Another strategy includes the development of novel, optimized, monoclonal antibodies capable of neutralizing Activin (or blocking its interaction with its receptor) used therapeutically to disrupt Treg populations and functions and increase the effectiveness of the anti-cancer immune response and anti-cancer immunotherapies. In some embodiments, antagonists of the factors directly up-regulated by Activin activity may also be used as tolerance breaking immunotherapies. Combinatorial strategies pairing Activin targeting agents with other treatment strategies (e.g., check point blockade, or anti-cancer vaccines, or chemotherapy) are also employed for improved anti-cancer effects. As described herein, inducers/agonists of Activin/Activin Receptor signaling may also be used as methods to increase Treg generation and subsequently promote immune tolerance to treat autoimmune and/or inflammatory diseases. In some embodiments, supplemental Activin may be used to support Tregs and immune tolerance, to treat autoimmune or inflammatory diseases, or to augment Treg populations for adoptive cell therapies intended to correct immune pathologies such as transplant/graft rejection.

Cancer

Cancers are a large family of diseases that involve abnormal cell growth with the potential to invade or spread to other parts of the body. They form a subset of neoplasms. A neoplasm or tumor is a group of cells that have undergone unregulated growth, and will often form a mass or lump, but may be distributed diffusely. Six characteristics of cancer have been proposed: self-sufficiency in growth signaling; insensitivity to anti-growth signals; evasion of apoptosis; enabling of a limitless replicative potential; induction and sustainment of angiogenesis; and activation of metastasis invasion of tissue. The progression from normal cells to cells that can form a discernible mass to outright cancer involves multiple steps known as malignant progression.

For example, the methods described herein are useful in treating various types of malignancies and/or tumors, e.g., non-Hodgkin's lymphoma (NHL), acute lymphocytic leukemia (ALL), acute myeloid leukemia (AML), chronic lymphocytic leukemia (CLL), chronic myelogenous leukemia (CML), multiple myeloma (MM), breast cancer, ovarian cancer, head and neck cancer, bladder cancer, melanoma, colorectal cancer, pancreatic cancer, lung cancer, leiomyoma, leiomyosarcoma, glioma, and glioblastoma. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

Cancerous, or neoplastic or hyperproliferative, cells have the capacity for autonomous growth—an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. Cancer, or neoplasm, includes malignancies of the various organ systems, such as those malignancies affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

Hematopoietic neoplastic disorders include diseases involving hyperplastic/neoplastic cells of hematopoietic origin, e.g., arising from myeloid, lymphoid or erythroid lineages, or precursor cells thereof. Typically, the diseases arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Methods of Treating Diseases

Provided herein are methods of treating diseases, disorders or conditions associated with cancer. The inventors have developed methods and products for treating cancer. The methods break immune tolerance and permit a robust anti-tumor immune response to be mounted by the subject. A combination of agents is used produce a strong suppression of tumor growth.

Agents may be administered by any suitable means known in the art. The agents may be administered systemically, if appropriate. Administration methods which may be used include without limitation intramuscular, intravenous, intraspinal, oral, sublingual, intracranial, intraperitoneal, inhalational, transdermal, subcutaneous and intratumoral.

Compositions of the present invention are administered to subjects in a variety of routes including but not limited to: oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

Compositions of the present invention are administered to subjects in a variety of forms including but not limited to: pills, capsules, tablets, granules, powders, salts, crystals, liquids, serums, syrups, solutions, emulsions, suspensions, gels, creams, pastes, films, patches, and vapors.

Immunotherapy

In some embodiments, the present invention provides for methods of treating cancer based on immunotherapy Immunotherapy is the treatment of disease by inducing, enhancing, or suppressing an immune response Immunotherapies designed to elicit or amplify an immune response are classified as activation immunotherapies, while immunotherapies that reduce or suppress are classified as suppression immunotherapies.

Cancer immunotherapy (immuno-oncology) is the use of the immune system to treat cancer. Immunotherapies fall into three main groups: cellular, antibody and cytokine. They exploit the fact that cancer cells often have subtly different molecules on their surface that can be detected by the immune system. These molecules, known as cancer antigens, are most commonly proteins, but also include molecules such as carbohydrates Immunotherapy is used to provoke the immune system into attacking the tumor cells by using these antigens as targets.

Immunotherapeutic agents are any that work through the immune system. These include antibodies and vaccines. Agents which stimulate the formation of a specific T cell or B cell response include vaccines. Antibodies may function by binding to target antigens and recruiting other members of the immune system such as complement to degrade the target antigen and/or cells that express them. Bispecific T cell engaging molecules recruit T cells to a target antigen. Cytokines can activate or inhibit parts of the immune system. Particular immunotherapeutic agents which can be used advantageously in the combinations of the invention include immune checkpoint inhibitors, anti-PD1 antibodies, anti-CTLA4 antibodies, anti-tumor vaccines, GVAX vaccines for lung, pancreas, leukemia, breast, sarcoma, melanoma and renal cancer carcinoma. Other vaccines and antibodies, such as tumor antigen peptide vaccines and antibodies to tumor antigens, can be used as well.

Compositions may comprise two or more agents, an Activin signaling modulator and an immunotherapeutic agent, in admixture. They can be mixed together by a manufacturer, by a pharmacist, by a clinician. The compositions may be formed in the body when administered close enough in time so that the first agent has not been totally cleared from the body before the second agent is administered. The two or more agents may be made in tandem as a fusion or conjugate molecule.

The two or more agents which are administered to the subject may but need not be administered simultaneously. If administered simultaneously, they may or may not be administered as an admixture. The two or more agents may also be administered separately within 2 days of each other, within 1 week of each other, or within 1 month of each other.

Antibody therapies are the most successful immunotherapy, treating a wide range of cancers. Antibodies are proteins produced by the immune system that bind to a target antigen on the cell surface. In normal physiology, the immune system uses antibodies to fight pathogens. Each antibody is specific to one or a few proteins. Those that bind to cancer antigens are used to treat cancer. Cell surface receptors, e.g., CD20, CD274, and CD279, are common targets for antibody therapies. Once bound to a cancer antigen, antibodies can induce antibody-dependent cell-mediated cytotoxicity, activate the complement system, or prevent a receptor from interacting with its ligand, all of which can lead to cell death. Multiple antibodies are approved to treat cancer, including Alemtuzumab, Ipilimumab, Nivolumab, Ofatumumab, and Rituximab.

Antibodies to Activin may be used as Activin inhibitors. Examples of Activin antibodies that can be purchased from R&D Systems include: Human/Mouse/Rat Activin A beta A subunit Antibody (catalog number MAB3381), Human Activin A Precursor Antibody (catalog number MAB1203). Examples of Activin antibodies from Santa Cruz Biotechnology include: Activin Antibody (D-82) (catalog number sc-98940). Examples of Activin antibodies that can be purchased from Sigma-Aldrich include: Anti-Activin A Antibody produced in goat (catalog number A1594). Examples of Activin antibodies that can be purchased from Novus Biologicals include: Activin A Antibody—beta A subunit (catalog number AF338). Examples of Activin antibodies that can be purchased from Abcam include: anti-Activin A Antibody [MM0074-7L18] (catalog number ab89307).

Alternatively, antibodies to Activin Receptor (ACVR1C or ALK7) may be used as Activin inhibitors. Examples of Activin Receptor antibodies that can be purchased from R&D Systems include human ALK-7 antibody (catalog number MAB7749) and human ALK-7 antibody (catalog number MAB77491). An example of an anti-ACVR1C polyclonal antibody from ThermoFisher Scientific includes catalog number PAS-48090. An example of an anti-ALK7 antibody from EMD Millipore includes catalog number 09-158.

Cellular therapies, also known as cancer vaccines, usually involve the removal of immune cells from the blood or from a tumor Immune cells specific for the tumor are activated, cultured and returned to the patient where the immune cells attack the cancer. Cell types that can be used in this way are natural killer cells, lymphokine-activated killer cells, cytotoxic T cells and dendritic cells.

Interleukin-2 and interferon-a are examples of cytokines, proteins that regulate and coordinate the behavior of the immune system. They have the ability to enhance anti-tumor activity and thus can be used as cancer treatments. Interferon-a is used in the treatment of hairy-cell leukemia, AIDS-related Kaposi's sarcoma, follicular lymphoma, chronic myeloid leukemia and malignant melanoma. Interleukin-2 is used in the treatment of malignant melanoma and renal cell carcinoma.

Immunotherapy may also involve targeting immune checkpoints to treat disease. Immune checkpoints are molecules in the immune system that either turn up a signal (co-stimulatory molecules) or turn down a signal. Many cancers protect themselves from the immune system by inhibiting the T cell signal. Inhibitory checkpoint molecules have been increasingly considered as new targets for cancer immunotherapies due to the effectiveness of two checkpoint inhibitor drugs that were initially indicated for advanced melanoma.

Stimulatory checkpoint molecules representing targets of immunotherapy include, but are not limited to: CD27, CD28, CD40, CD122, CD137, OX40, ICOS, and GITR. Four stimulatory checkpoint molecules are members of the tumor necrosis factor (TNF) receptor superfamily—CD27, CD40, OX40, GITR and CD137. Another two stimulatory checkpoint molecules belongs to the B7-CD28 superfamily—CD28 itself and ICOS. CD27 supports antigen-specific expansion of naive T cells and is vital for the generation of T cell memory. CD27 is also a memory marker of B cells. CD27's activity is governed by the transient availability of its ligand, CD70, on lymphocytes and dendritic cells. CD27 costimulation is known to suppresses Th17 effector cell function. CD28 is constitutively expressed on almost all human CD4+ T cells and on around half of all CD8 T cells. Binding with its two ligands are CD80 and CD86, expressed on dendritic cells, prompts T cell expansion. CD28 was the target of the TGN1412 "superagonist" which caused severe inflammatory reactions in the first-in-man study. CD40 is found on a variety of immune system cells including antigen presenting cells and has CD40L (otherwise known as CD154 and transiently expressed on the surface of activated CD4+ T cells) as its ligand. CD40 signaling is known to cause dendritic cells to mature and thereby trigger T-cell activation and differentiation. CD122 is the Interleukin-2 receptor beta sub-unit, and is known to increase proliferation of CD8+ effector T cells. When CD137, also called 4-1BB, is bound by CD137 ligand, the result is T-cell proliferation. CD137-mediated signaling is also known to protect T cells, and in particular, CD8+ T cells from activation-induced cell death. OX40 (also called CD134) has OX40, or CD252, as its ligand. Like CD27, OX40 promotes the expansion of effector and memory T cells, however it is also noted for its ability to suppress the differentiation and activity of T-regulatory cells, and also for its regulation of cytokine production. OX40's value as a drug target primarily lies it the fact that, being transiently expressed after T-cell receptor engagement, it is only upregulated on the most recently antigen-activated T cells within inflammatory lesions. Anti-OX40 monoclonal antibodies have been shown to have clinical utility in advanced cancer. GITR (Glucocorticoid-Induced TNFR family Related gene) prompts T cell expansion, including Treg expansion. The ligand for GITR is mainly expressed on antigen presenting cells. Antibodies to GITR have been shown to promote an anti-tumor response through loss of Treg lineage stability. ICOS (Inducible T-cell costimulatory—also called CD278) is expressed on activated T cells. Its ligand is ICOSL, expressed mainly on B cells and dendritic cells. The molecule seems to be important in T cell effector function.

Inhibitory checkpoint molecules representing targets of immunotherapy include, but are not limited to: A2AR, B7-H3, B7-H4, BTLA, CTLA-4, IDO, KIR, LAGS, PD-1, TIM-3, and VISTA. A2AR (Adenosine A2A receptor) is regarded as an important checkpoint in cancer therapy because adenosine in the immune microenvironment, leading to the activation of the A2a receptor, is a negative immune feedback loop and the tumor microenvironment has relatively high concentrations of adenosine. B7-H3 (also called CD276) is regarded as co-inhibitory. B7-H4 (also called VTCN1) is expressed by tumor cells and tumor-associated macrophages and plays a role in tumor escape. BTLA (B and T Lymphocyte Attenuator—also called CD272) has HVEM (Herpesvirus Entry Mediator) as its ligand. Surface expression of BTLA is gradually downregulated during differentiation of human CD8+ T cells from the naive to effector cell phenotype, however tumor-specific human CD8+ T cells express high levels of BTLA. Expression of CTLA-4 (Cytotoxic T-Lymphocyte-Associated protein 4—also called CD152) on Treg cells serves to control T cell proliferation. IDO (Indoleamine 2,3-dioxygenase) is a tryptophan catabolic enzyme with immune-inhibitory properties. Another important molecule is TDO, tryptophan 2,3-dioxygenase. IDO is known to suppress T and NK cells, generate and activate Tregs and myeloid-derived suppressor cells, and promote tumor angiogenesis. KIR (Killer-cell Immunoglobulin-like Receptor) is a receptor for MHC Class I molecules on Natural Killer cells. LAGS (Lymphocyte Activation Gene-3) works to suppress an immune response via Tregs as well as directly through effects on CD8+ T cells. PD-1 (Programmed Death 1 (PD-1) receptor) has two ligands, PD-L1 and PD-L2. An advantage of targeting PD-1 is that it can restore immune function in the tumor microenvironment. TIM-3 (T-cell Immunoglobulin domain and Mucin domain 3) is expressed on activated human CD4+ T cells and regulates Th1 and Th17 cytokines. TIM-3 acts as a negative regulator of Th1/Tc1 function by triggering cell death upon interaction with its ligand, galectin-9. VISTA (V-domain Ig suppressor of T cell activation) is primarily expressed on hematopoietic cells so that consistent expression of VISTA on leukocytes within tumors may allow VISTA blockade to be effective across a broad range of solid tumors.

Combination Therapy

Compositions of the invention may be combined in a pharmaceutical combination formulation, or dosing regimen as combination therapy, with a second compound that has anti-hyperproliferative properties or that is useful for treating a hyperproliferative disorder (e.g. cancer). The second compound of the pharmaceutical combination formulation or dosing regimen preferably has complementary activities to the compounds of the invention such that they do not adversely affect the other(s). Such molecules are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities. Suitable dosages for any of the above coadministered agents are those presently used and may be lowered due to the combined action (synergy) of the newly identified agent and other chemotherapeutic agents or treatments.

The combination therapy may provide "synergy" and prove "synergistic", e.g. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, e.g. serially, whereas in combination therapy, effective dosages of two or more active ingredients are administered together.

As an example, the agent may be administered in combination with surgery to remove an abnormal proliferative cell mass. As used herein, "in combination with surgery" means that the agent may be administered prior to, during or after the surgical procedure. Surgical methods for treating epithelial tumor conditions include intra-abdominal surgeries such as right or left hemicolectomy, sigmoid, subtotal or total colectomy and gastrectomy, radical or partial mastectomy, prostatectomy and hysterectomy. In these embodiments, the agent may be administered either by continuous infusion or in a single bolus. Administration during or immediately after surgery may include a lavage, soak or perfusion of the tumor excision site with a pharmaceutical preparation of the agent in a pharmaceutically acceptable carrier. In some embodiments, the agent is administered at the time of surgery as well as following surgery in order to inhibit the formation and development of metastatic lesions. The administration of the agent may continue for several hours, several days, several weeks, or in some instances, several months following a surgical procedure to remove a tumor mass.

The subjects can also be administered the agent in combination with non-surgical anti-proliferative (e.g., anti-cancer) drug therapy. In one embodiment, the agent may be administered with a vaccine (e.g., anti-cancer vaccine) therapy. In one embodiment, the agent may be administered in combination with an anti-cancer compound such as a cytostatic compound. A cytostatic compound is a compound (e.g., a nucleic acid, a protein) that suppresses cell growth and/or proliferation. In some embodiments, the cytostatic compound is directed towards the malignant cells of a tumor. In yet other embodiments, the cytostatic compound is one that inhibits the growth and/or proliferation of vascular smooth muscle cells or fibroblasts.

Suitable anti-proliferative drugs or cytostatic compounds to be used in combination with the agents of the invention include anti-cancer drugs. Anti-cancer drugs are well known and include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine;. Methotrexate; Methotrexate Sodium; Metoprine;.Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine;. Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin;. Streptozocin; Sulofenur; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride;

Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinflunine; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

According to the methods of the invention, the agents of the invention may be administered prior to, concurrent with, or following the other anti-cancer compounds or therapies. The administration schedule may involve administering the different agents in an alternating fashion. In other embodiments, the agent may be delivered before and during, or during and after, or before and after treatment with other therapies. In some cases, the agent is administered more than 24 hours before the administration of the other anti-proliferative treatment. In other embodiments, more than one anti-proliferative therapy may be administered to a subject. For example, the subject may receive the agents of the invention, in combination with both surgery and at least one other anti-proliferative compound. Alternatively, the agent may be administered in combination with more than one anti-cancer drug.

Pharmaceutical Compositions

In certain embodiments, the present invention provides for a pharmaceutical composition comprising an agent employed in the present invention. The agent can be suitably formulated and introduced into a subject or the environment of a cell by any means recognized for such delivery.

Such compositions typically include the agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The compositions of the invention could also be formulated as nanoparticle formulations. The compounds of the invention can be administered for immediate-release, delayed-release, modified-release, sustained-release, pulsed-release and/or controlled-release applications. The pharmaceutical compositions of the invention may contain from 0.01 to 99% weight-per volume of the active material. For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For a compound used in a method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an agent (i.e., an effective dosage) depends on the agent selected. For instance, single dose amounts of an agent in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered.

A therapeutically effective amount of the compound of the present invention can be determined by methods known in the art. In addition to depending on the agent and selected/ pharmaceutical formulation used, the therapeutically effective quantities of a pharmaceutical composition of the invention will depend on the age and on the general physiological condition of the patient and the route of administration. In certain embodiments, the therapeutic doses will generally be between about 10 and 2000 mg/day and preferably between about 30 and 1500 mg/day. Other ranges may be used, including, for example, 50-500 mg/day, 50-300 mg/day, 100-200 mg/day.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an agent can include a single treatment or, optionally, can include a series of treatments.

It can be appreciated that the method of introducing an agent into the environment of a cell will depend on the type of cell and the makeup of its environment. Suitable amounts of an agent must be introduced and these amounts can be empirically determined using standard methods. Exemplary effective concentrations of an individual agent in the environment of a cell can be 500 millimolar or less, 50 millimolar or less, 10 millimolar or less, 1 millimolar or less, 500 nanomolar or less, 50 nanomolar or less, 10 nanomolar or less, or even compositions in which concentrations of 1 nanomolar or less can be used.

The pharmaceutical compositions can be included in a kit, container, pack, or dispenser together with instructions for administration.

This invention is further illustrated by the following examples which should not be construed as limiting. The contents of all references, patents, and published patent applications cited throughout this application, as well as the figures, are incorporated herein by reference.

EXAMPLES

Example 1

Activin and Its Receptor are Expressed by Tregs

Figure 1A:
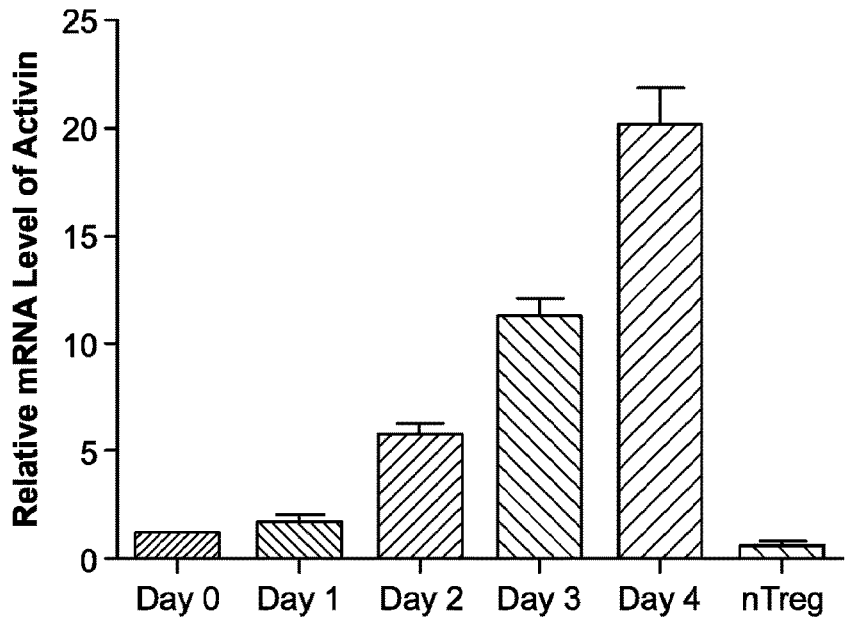
FIG. 1A-FIG. 1C shows graphs depicting how both Activin A and its receptor (ACVR1C) are upregulated during the course of iTreg differentiation. Naïve T cells sorted from C57BL/6 mice, and cultured under iTreg skewing condition: anti-CD3 (4 ug/ml), anti-CD28 (2 ug/ml), TGF-β 5 ng/ml, IL2 100 IU/ml for the indicated period of time. Freshly isolated nTregs were also collected for analysis. The indicated cells were collected and subjected to RNA extraction, followed by qRT-PCR analysis for mRNA expression of Activin (FIG. 1A), Foxp3 (FIG. 1B), and Activin Receptor (ACVR1C) (FIG. 1C).

Suspecting that Activin might play a significant role in promoting immune tolerance by affecting Tregs, levels of Activin mRNA were measured across diverse CD4+ T cells subsets by RTPCR. Substantial levels were found in Treg subsets. While Activin levels were low in naïve CD4+ T cells, in vitro differentiating Tregs (naïve CD4+ T cells activated with anti-CD3/CD28 in the presence of IL-2 and TGF-β) up-regulated Activin expression over time (FIG. 1A). The kinetics of this up-regulation paralleled the appearance of Foxp3 expression in these cells (FIG. 1C).

Figure 1B:
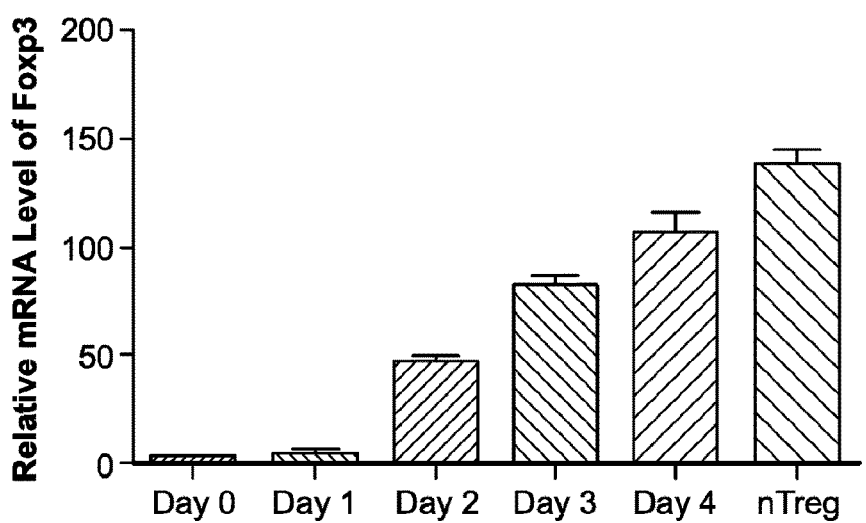
Figure 1C:
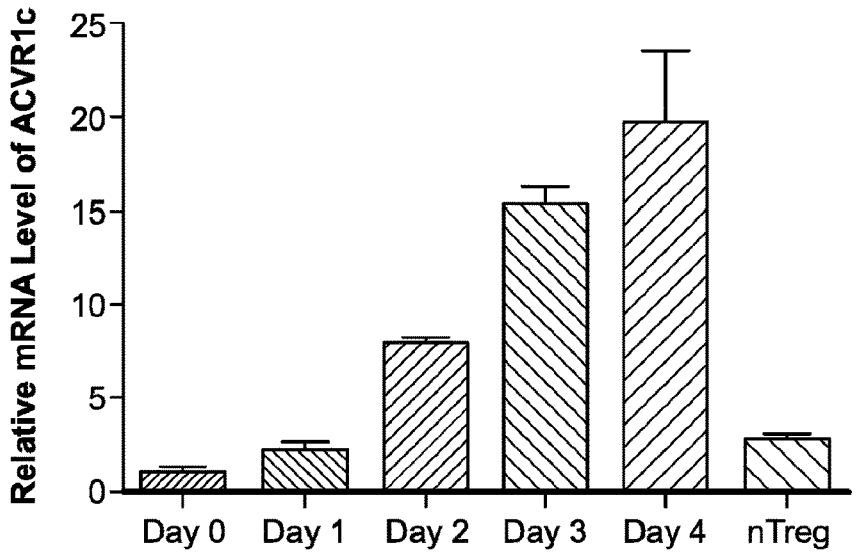

RTPCR analysis also showed that expression of the Activin Receptor (ACVR1C) was similarly low in naïve CD4+ T cells, but robustly up-regulated during differentiation towards an induced Treg fate (FIG. 1B). Isolated nTregs were found to express only marginal levels of these genes at baseline. However their expression dramatically increased upon activation (FIG. 1A-FIG. 1C). This suggests that Activin A expression and responsiveness may have considerable influence over the biology of Tregs.

Example 2

Enhancement of SMAD/TGF-β Signaling and Treg Differentiation by Activin

Figure 2A:
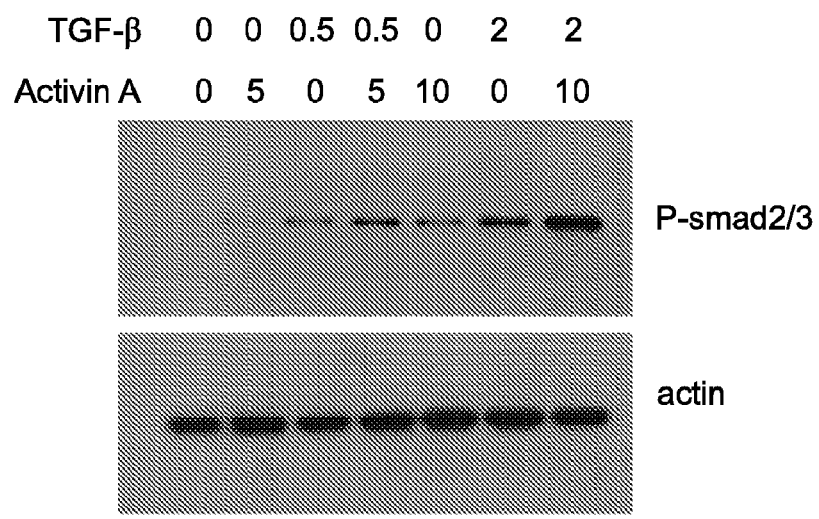
FIG. 2A and FIG. 2B is a series of immunoblots and histograms demonstrating that YAP/Activin/ACVR1C pathway enhances Smad2/3 activation, Treg generation and function, and tumor progression.

Since Activin has been reported to promote SMAD signaling in non-T cells (Schmierer, B., et al., J Biol Chem, 2003. 278:21197-203), whether Activin signaling in T cells could have a similar effect was examined SMAD activity was assessed by western blot analysis of SMAD phosphorylation. Indeed, while untreated CD4+ T cells did not contain discernable levels of active (phosphorylated) SMAD molecules, treatment with 5 or 10 ng/ml of Activin resulted in elevation of phospho-SMAD. TGF-βtreatment (0.5 or 2 ng/ml) also induced SMAD phosphorylation. Combined Activin and TGF-β treatment saw even further activation of the SMAD signaling pathway (FIG. 2A). These findings suggest that Activin signaling can augment signaling along the TGF-β/SMAD axis—a signaling pathway crucial for multiple aspects of Treg biology and immune tolerance (Tran, D. Q., J Mol Cell Biol, 2012. 4:29-37).

Figure 2B:
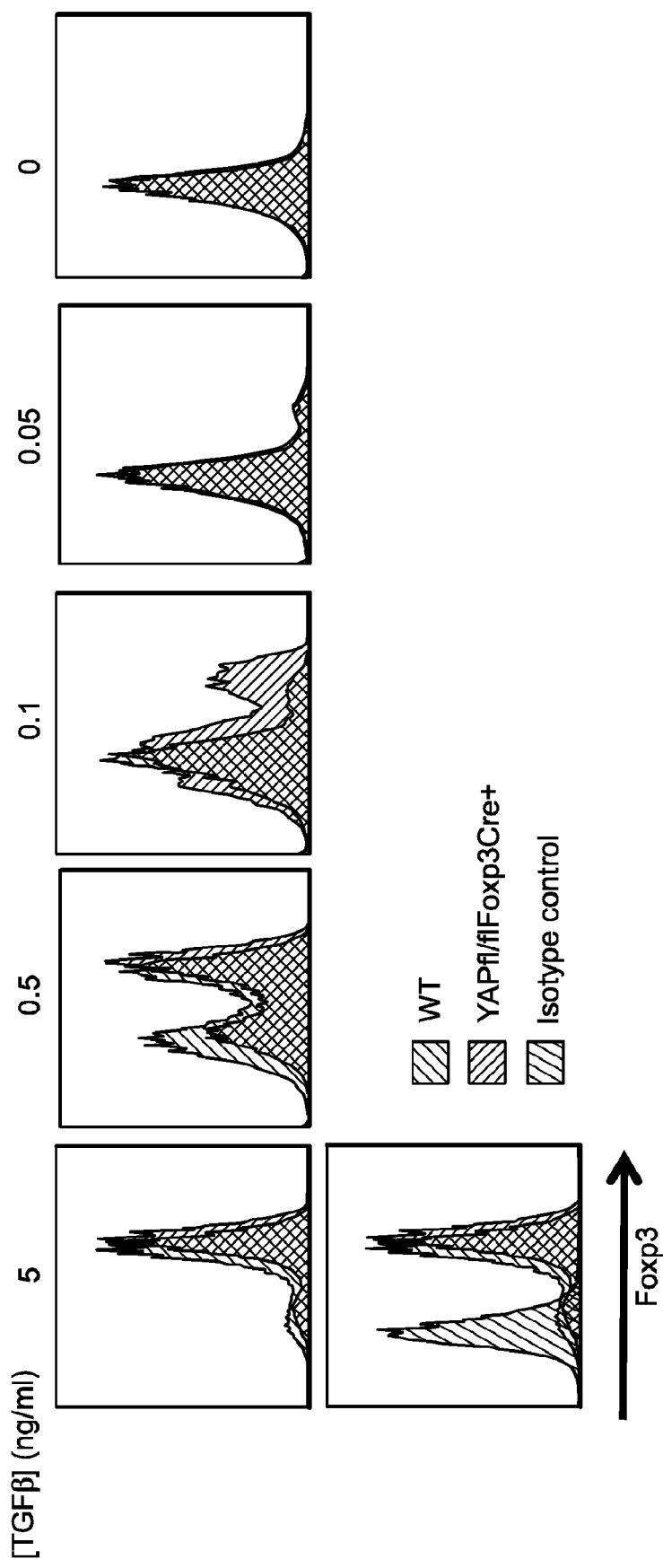

Since TGF-β/SMAD mediated events are important during the up-regulation of Foxp3 and the generation of Tregs from naïve CD4+ T cell precursors, whether YAP-dependent Activin signaling can participate in driving this process was investigated. Initially, the ability of YAP-deficient T cells to differentiate into Tregs by up-regulating Foxp3 was compared in vitro. As demonstrated in FIG. 2B, in the presence of suboptimal TGFβ levels, YAP plays an important role in promoting Foxp3 expression. YAP-mediated upregulation of ACVR1C and SMAD2 may provide a crucial amplification of meager SMAD2 signaling that allows for sustained Foxp3 expression.

Figure 3:
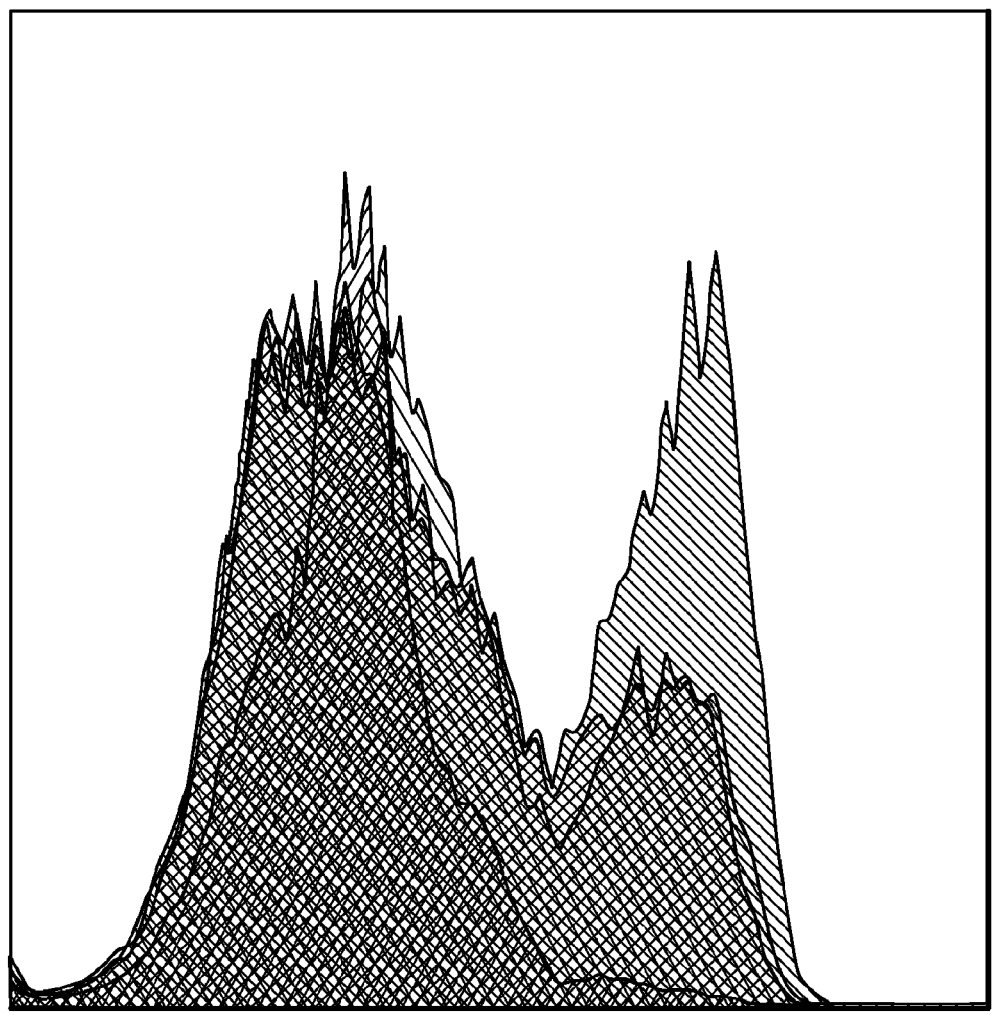
FIG. 3 is a histogram demonstrating that Activin treatment induces Foxp3 and synergizes with TGF-beta. Naïve CD4+ T cells from Yap1f/f,Foxp3-yfpCre+ (KO) and Yap1 wt/wt,Foxp3ypfCre+ (WT) mice were stimulated with anti-CD3/CD28 antibodies (1 and 4 ug/ml, respectively) for 3 days in the presence of IL-2 (100 U/ml) and the indicated doses of TGFβ and exogenous Activin A. A low dose of TGF-beta and/or activin was also administered to the indicated samples (activin was dosed at 50 ng/ml on day 0 and day 2 of culture). Treg induction (via detection of intracellular Foxp3 up-regulation) was determined by flow cytometry.

To explore the involvement of Activin/ACVR1C signaling in the driving of Treg differentiation by YAP, the effects of supplemental Activin on in vitro Treg commitment was also investigated. Activation of wild type naïve CD4+ T cells without TGFβ yielded little-to-no Foxp3 induction. Strikingly, activation of these cells with exogenous Activin A, even in the absence of TGFβ, generated a population of Foxp3+ cells. While a suboptimal concentration of TGF-β resulted in modest up-regulation of Foxp3 (mirroring the effects on SMAD activation), combined treatment of wild type naïve CD4+ T cells with low doses of TGF-β+ Activin resulted in synergistic promotion of Foxp3+ T cell induction. This induction of Tregs by Activin treatment alone was not seen upon Foxp3-driven knockout of YAP, and while dual treatment of differentiating Foxp3yfpere+/Yap1f/f iTregs did enhance the generation of Foxp3+ cells, this was to an extent far less than that seen in their wild type counterparts (FIG. 3).

Without TGF-β, Foxp3 induction was minimal. A suboptimal concentration of TGF-β resulted in a modest up-regulation of Foxp3. Treatment of naïve CD4+ T cells with exogenous Activin, even in the absence of TGF-β, resulted in a comparable population of Foxp3+ cells. Furthermore, combined treatment with Activin and TGFβ treatment resulted in synergistic promotion of Foxp3+ T cell induction (FIG. 3). These results suggest that Activin cannot only augment TGF-βsignaling, but also the Treg pool.

Example 3

Antibody Mediated Activin Blockade Inhibits Tumor Growth as Monotherapy or in Combination with Checkpoint Blockade Having clearly demonstrated the positive effects of Activin signaling on the TGFβ/SMAD signaling pathway and the process of Treg generation—both decidedly tolerance-promoting outcomes—disruption of Activin function should have an opposite effect.

While Tregs are necessary to maintain immune homeostasis, they pose an obstacle for mounting effective anti-tumor immune responses, and their suppressive function dampens the efficacy of anti-cancer immunotherapies. For these reasons, therapies aimed at undermining Treg-enforced tolerance are being investigated as potential additions to the cancer-fighting arsenal (Klages, K., et al., Cancer Res, 2010. 70:7788-99). Based on the amplification of the Treg-promoting TGF-β/SMAD signaling pathway by Activin, targeting this molecule could significantly interfere with Treg-mediated suppression of the anti-tumor immune response.

As an instigator of an apparent feed-forward loop capable of amplifying TGF-β/SMAD activity, YAP presents a tempting target for those aiming to break tolerance in the cancer setting. However, the targeting of YAP in cancer patients may prove problematic owing to the molecule's intracellular location and the chemical drawbacks of known inhibitors (e.g. solubility issues). Therefore, the Activin/ACVR1C interaction serves as a desirable alternative strategy. Having demonstrated the positive effects of Activin signaling on the TGFβ/SMAD signaling pathway and the processes of Treg generation and function—all of which are suppressive of anti-tumor immunity—disrupting Activin function enhanced anti-tumor immunity.

Figure 4:
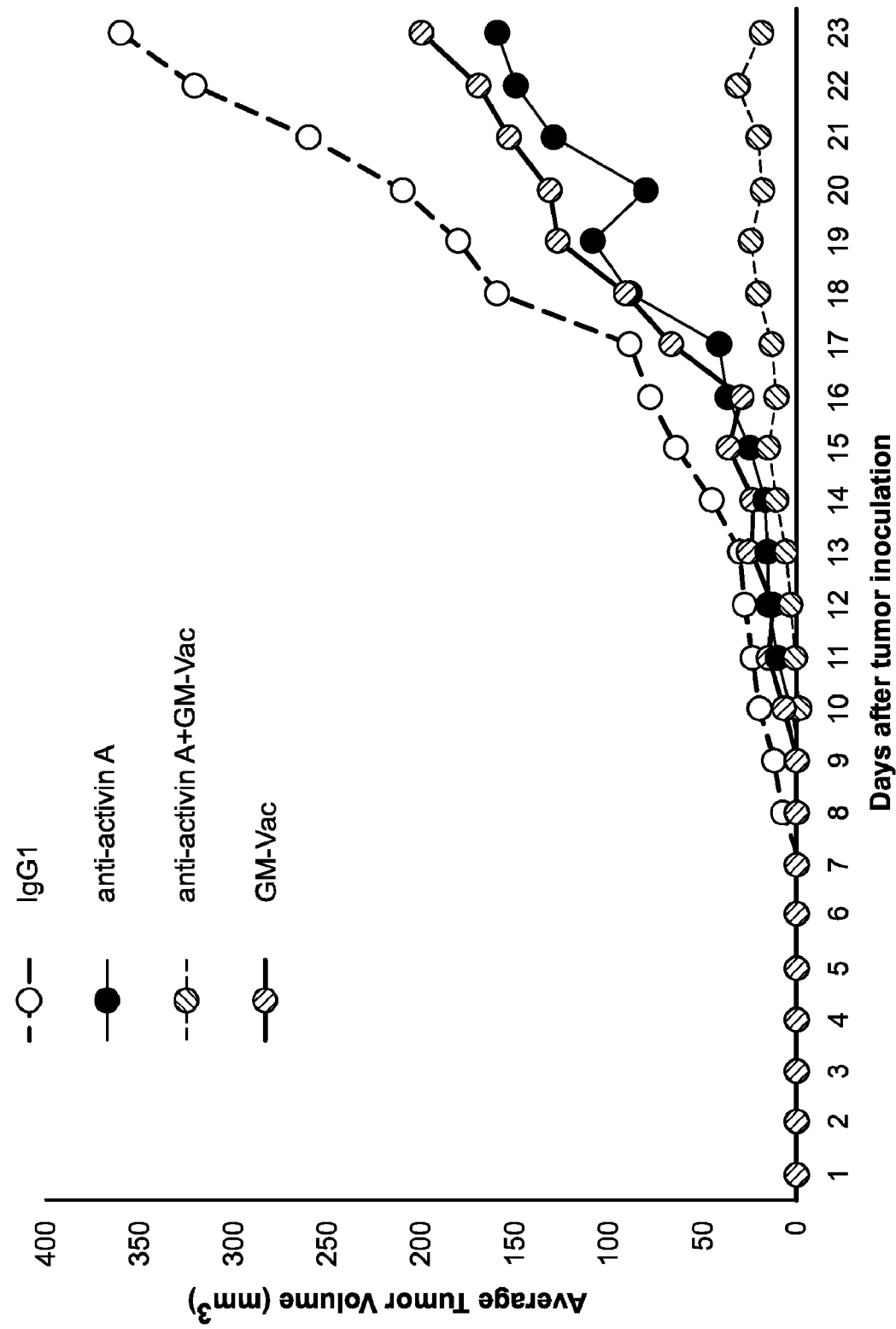
FIG. 4 is a graph demonstrating that Activin neutralizing antibodies together with GM-vac significantly stunt B16 tumor growth. $2 \times 10^4$ B16 melanoma cells were injected into individual C57BL/6 mice. Anti-activin A antibodies were purchased from R&D. 100 µg/mouse/injection of anti-activin A was administered intraperitoneally twice a week once tumors were palpable (7-10 days). Other cohorts of tumor-bearing mice received GM-vaccine (100 µl of 1×106 lethally irradiated (150Gy) B16 GM-vaccine cells or combined anti-Activin/GM-vaccine treatment. Tumors were measured daily and volume was calculated by the formula: Length (mm)×Width (mm)×Height (mm)×0.5326×0.01. n=10 mice per group.

The therapeutic potential of Activin targeting as an immunotherapeutic approach to combat cancer was tested. Administration of anti-Activin monoclonal antibody (purchased from R&D Systems) to mice injected subcutaneous B16 melamonas markedly stunted the development of tumors relative to an inert isotype control (FIG. 4). Activin neutralization antibodies and isotype control IgG were purchased from R&D Systems (catalogue number: MAB3381). 100 μg/mouse/injection of activin neutralization antibodies was given intraperitoneally twice a week.

Some of the most promising immunotherapeutic agents (i.e. PD-1 and CTLA-4 antagonist antibodies) show even greater anti-tumor effect when administered in concert (Curran, M. A., et al., Proc Natl Acad Sci U S A, 2010. 107:4275-80) or alongside tumor vaccine strategies (Duraiswamy, J., et al., Cancer Res, 2013. 73:3591-603). The value of combining anti-Activin blocking antibody treatment with an anti-cancer vaccine (generated by irradiating GMCSF-producing B16 cells, "GM-Vac") was examined. Treatment with GM-Vac alone was able to slow the growth of tumors to an extent similar to anti-Activin monotherapy. However, combining anti-Activin treatment with GM-Vac was able to arrest tumor growth at a barely detectable size (FIG. 4).

Example 4

YAP Potentiates Expression of Genes Involved in TGFβ/SMAD Signaling

Figure 5A:
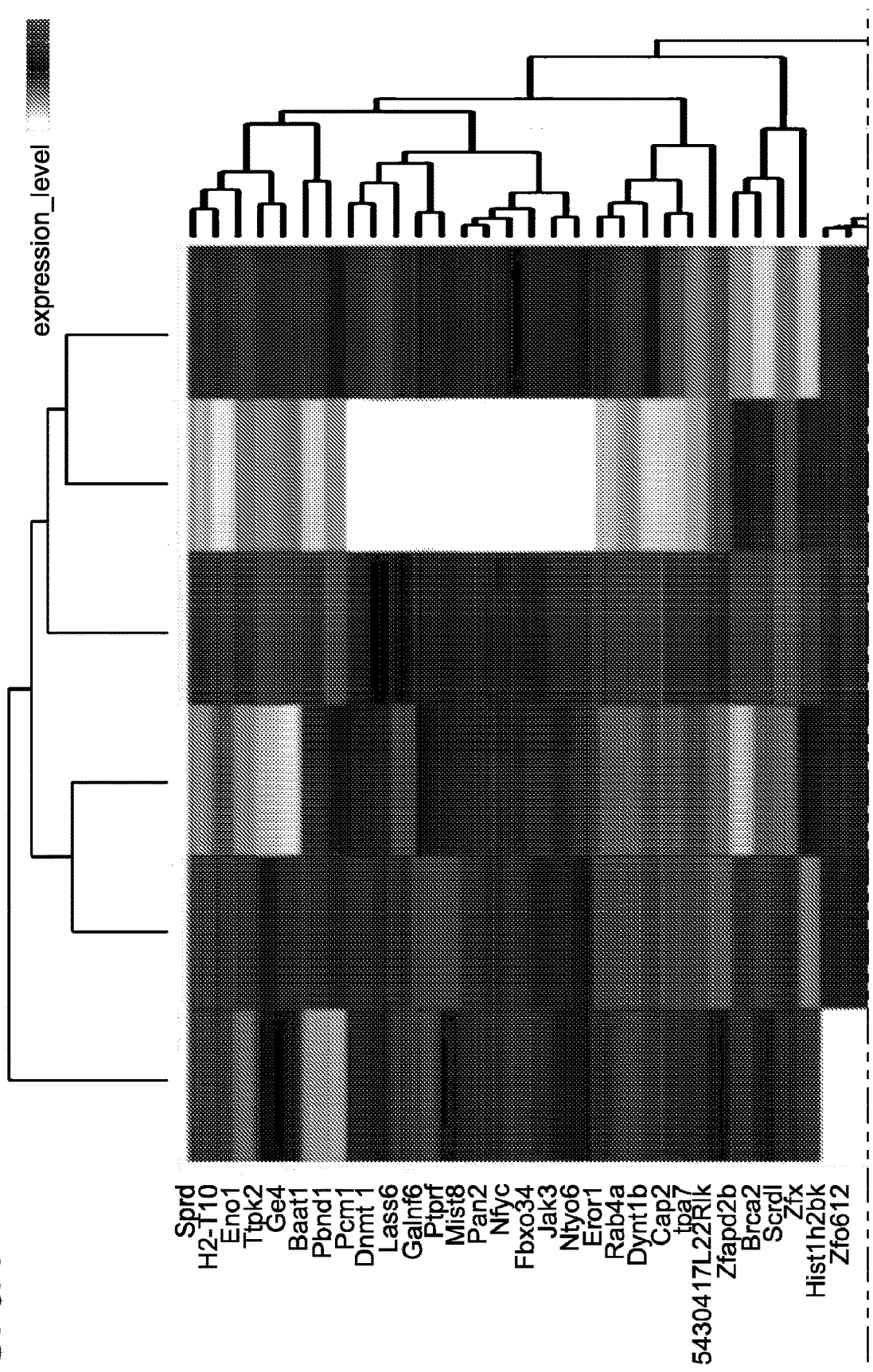
FIG. 5A and FIG. 5B demonstrate how RNASeq analysis was used to compare the transcriptomes of wild type and YAP-deficient Tregs.
Figure 5A:
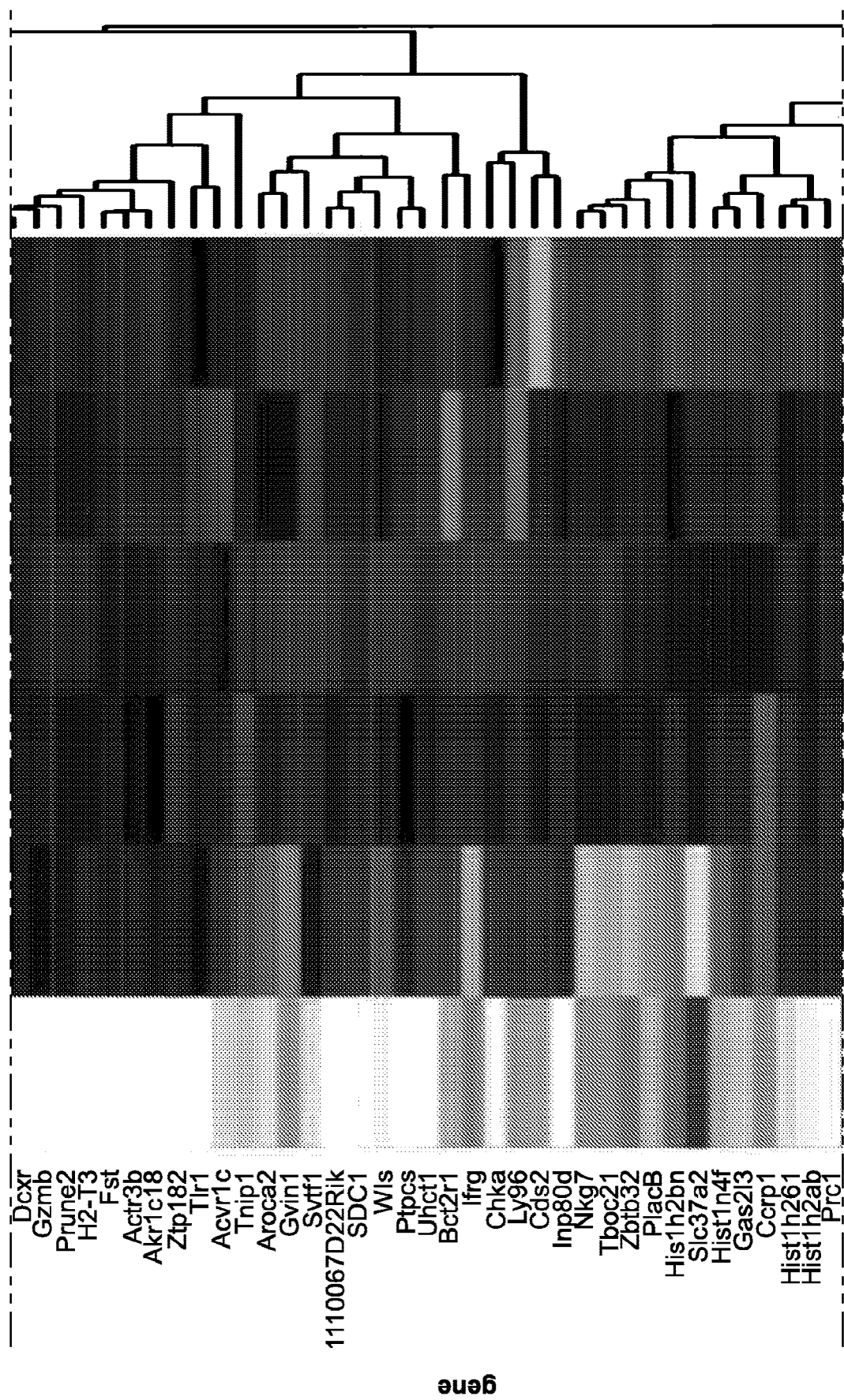
Figure 5A:
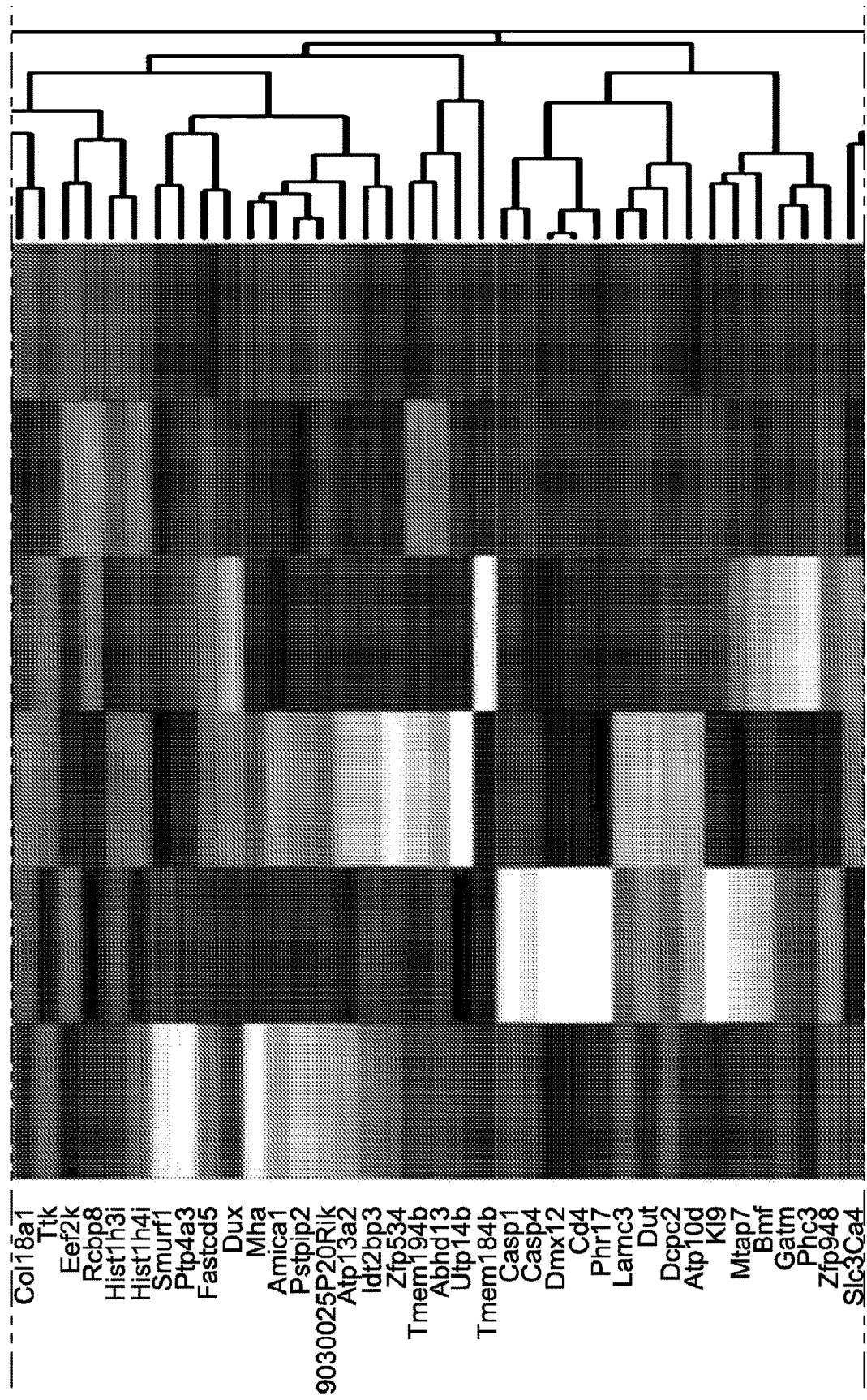
Figure 5A:
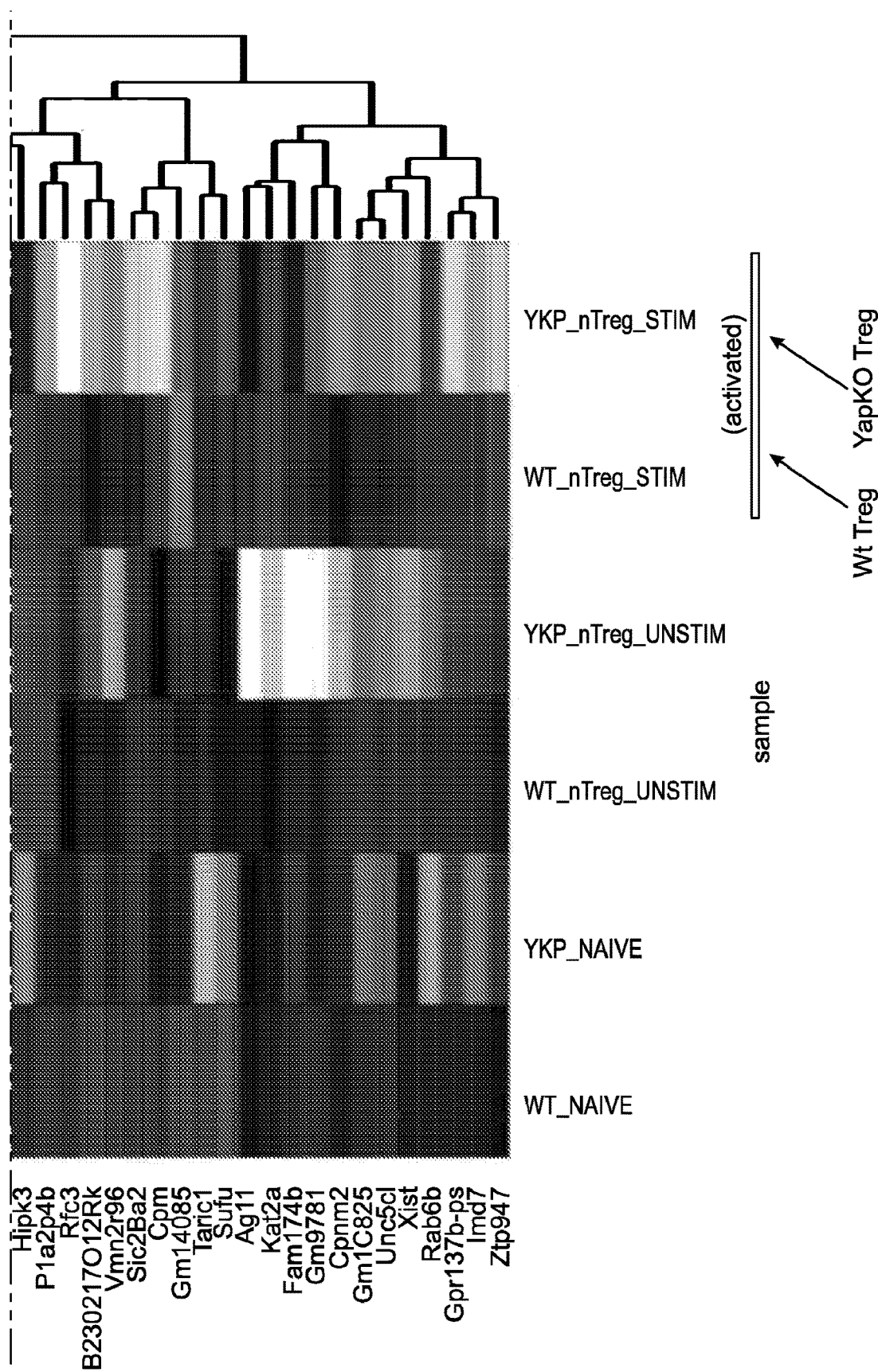

To gain insight into the mechanism by which YAP contributes to Tregs and their enforcement of immune suppression, Tregs were isolated from mice lacking YAP specifically (Foxp3yfpere+/Yap1f/I) and the Tregs were subjected to RNASeq analysis along with wild type Tregs (Foxp3yfpere+/Yap1 wt/wt). The results of this analysis revealed that YAP-deficient Tregs display reduced expression of several genes known to be important in the signaling pathway triggered by the anti-inflammatory cytokine TGFβ. One of the genes most down-regulated in the absence of YAP was the receptor for Activin (ACVR1C) (FIG. 5A). As described herein, Activin promotes TGFβ signaling. YAP contributes to Treg-mediated immune control by bolstering TGFβ/SMAD signaling through the Activin/ACVR1C axis.

Figure 5B:
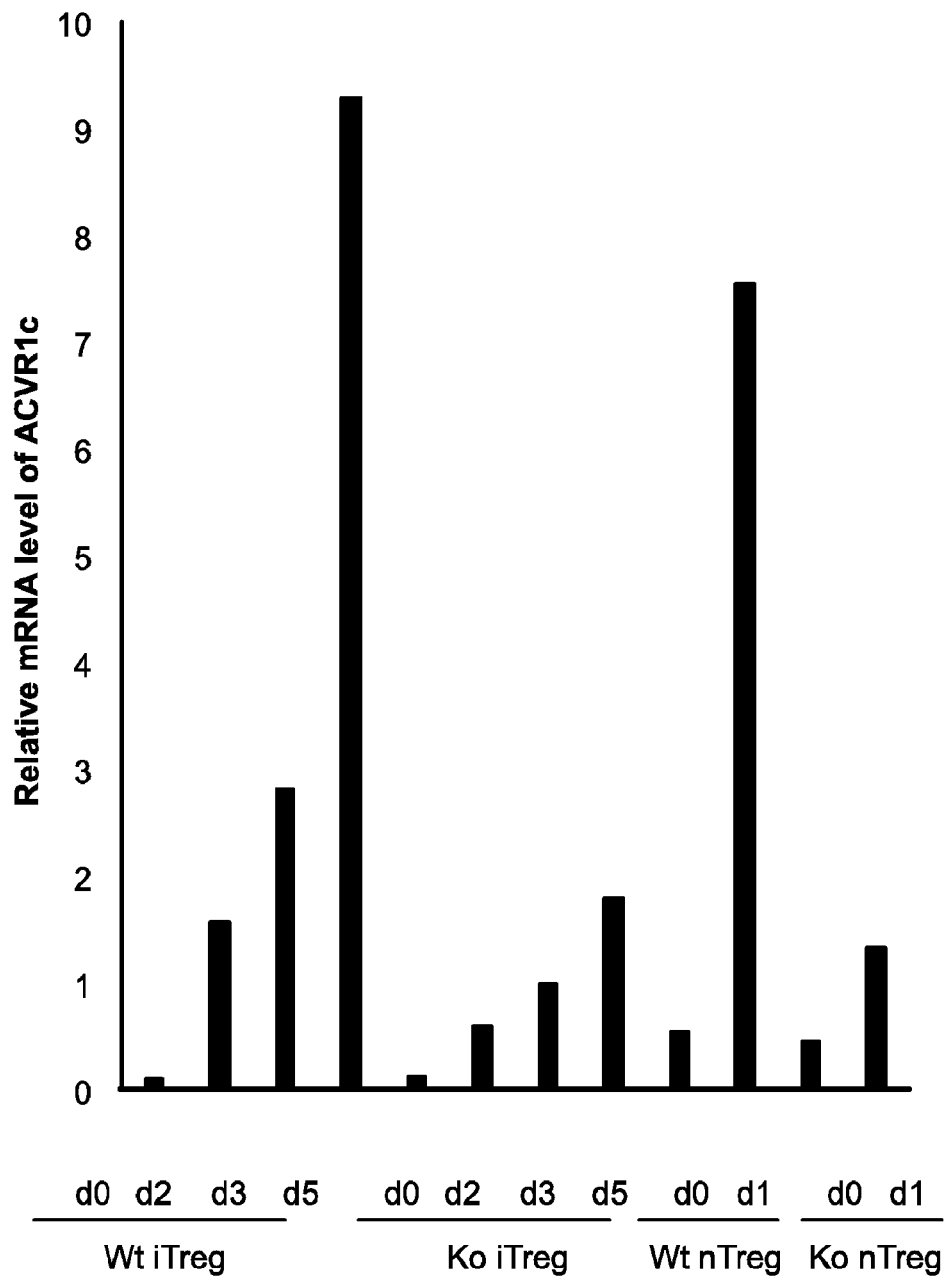

Measurement of Activin mRNA levels across diverse CD4+ T cells subsets by qRT-PCR revealed that Activin is substantially expressed in Treg subsets. While Activin levels were low in naïve CD4+ T cells, in vitro differentiating Tregs (naïve CD4+ T cells activated with anti-CD3/CD28 in the presence of IL-2 and TGF-β) up-regulated Activin expression over time (as seen in FIG. 1A). The kinetics of this up-regulation paralleled the appearance of Foxp3 expression in these cells (as seen in FIG. 1C).

qRT-PCR analysis also showed that expression of the Activin Receptor (ACVR1C) was similarly low in naïve CD4+ T cells, but robustly up-regulated under in vitro culture conditions that generate iTreg (FIG. 5B and FIG. 1B). Isolated nTregs were found to express only marginal levels of this gene at baseline. However ACVR1C expression dramatically increased upon activation. Neither nTreg nor differentiating iTregs from Foxp3yfpere+/Yap1f/f mice expressed considerable ACVR1C mRNA levels (FIG. 5B). This suggests that Activin A expression and responsiveness may have considerable influence over the biology of Tregs.

Example 5

Activin-Mediated Support of Treg Function is YAP/ACVR1C-Dependent

Figure 6:
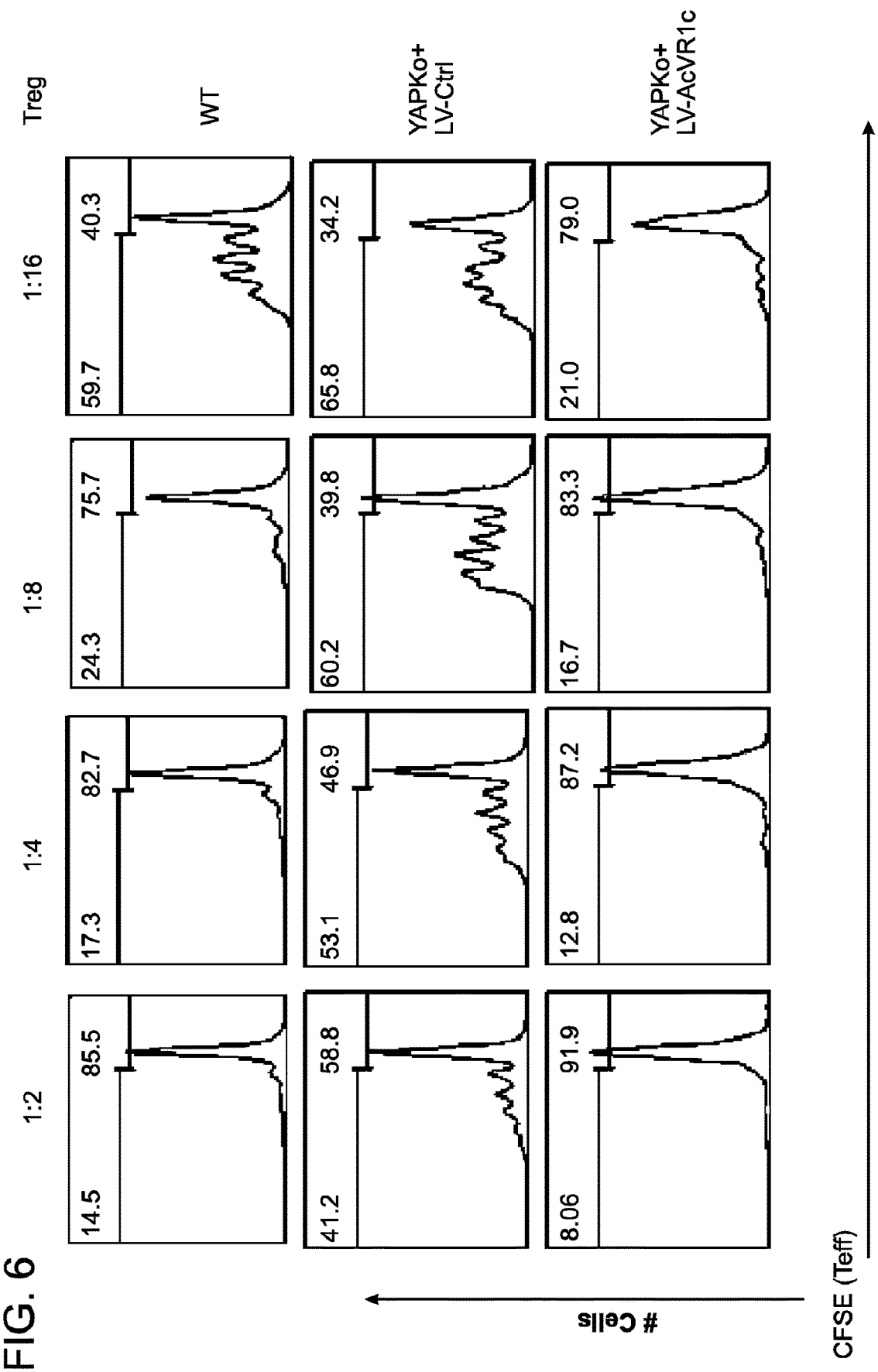
FIG. 6 is a series of histograms demonstrating that YAP/Activin/ACVR1C pathway enhances SMAD activation, Treg generation and function, and tumor progression. Following lentiviral delivery of an ACVR1C over-expression construct or an empty vector control construct to WT and YAPfl/flFoxp3Cre+Tregs (activated ex vivo overnight with anti-CD3/CD28 antibodies and IL-2), the functional capacity of these cells were assessed in vitro.

YAP deficiency leads to improved anti-tumor immunity and a Treg pool that is insensitive to an activator of the TGF-β/SMAD signaling pathway (i.e., Activin). YAP facilitates robust Treg function in vivo through the induction of ACVR1C, which in turn amplifies the pro-Treg signaling cascades. In order to determine if the Treg-promoting effects of YAP were due to the up-regulation of ACVR1C, whether the defective Treg function seen in YAP knockouts could be restored by ectopic expression of ACVR1C was examined. In an in vitro suppression assay, Foxp3yfpere+/Yap1f/f derived Tregs transduced with an empty vector control were much less efficient suppressors of naïve CD4+ T cell proliferation than the wild type counterparts. However, lentiviral delivery of an ACVR1C-encoding expression construct into Foxp3yfpere+/Yap1f/f derived Tregs greatly enhanced their suppressive potency beyond even that of wild type Tregs (FIG. 6).

Analysis of downstream targets of YAP activity in Treg identified ACVR1C and led to the finding that the Activin-Activin Receptor signaling axis plays a major role in the augmentation of TGF-β/SMAD signaling and Treg generation and function (summarized in FIG. 7). This pathway is highly important for the induction of extrathymic Foxp3+ T cells from naïve CD4+ precursors as SMADS bind critical enhancer regions for the Foxp3 gene (Zheng, Y., et al., Nature, 2010. 463:808-12; Josefowicz, S. Z., et al., Nature, 2012. 482:395-9). It is also important for sustaining Foxp3 expression and suppressive function in Tregs, generally (Tran, D. Q., J Mol Cell Biol, 2012. 4:29-37).

RNAseq and qRTPCR analysis showed that activin receptor 1c (ACVR1C) was significantly down-regulated in Tregs lacking YAP. Exposure to Activin resulted in amplification of TGFβ signaling and Foxp3 induction in wt but not YAP-/- Treg. Forced expression of ACVR1c by YAP-/- Tregs could rescue suppressive activity. Furthermore, Activin blockade slowed tumor growth and improved the effectiveness of an anti-tumor vaccine in an aggressive, poorly immunogenic mouse model of melanoma. Therapeutic disruption of the activin/ACVR1C axis can yield superior anti-tumor immunity.

These results support the conclusion that Activin can support the TGFβ-driven induction of Tregs and potentially other broadly immune-suppressing effects of this cytokine. The results presented herein also suggest that targeting either YAP or Activin signaling undermines the tolerance promoting attributes of TGFβ and both subsets of Foxp3+ Treg cells in the cancer setting—either alone, or in combination with other promising immunotherapeutic agents. Antibody mediated Activin blockade may prove a most effective means for the disruption of Treg- and tumor-abetting TGF-β activation in cancer patients. As described herein, antibodies capable of neutralizing activin or blocking its association with ACVR1C in cancer patients lead to new and potent immunotherapeutic regiments to unleash anti-tumor immunity from stifling Treg-enforced tolerance. On the other hand, as described herein, supplementation of activin or other therapeutic enhancements of the Activin/ACVR1C axis is a strategy to correct inadequate immune regulation in settings of autoimmune (MS) or inflammatory disease (IBD).

It is known that serum levels of Activin are elevated during pregnancy—a state during which there is a need for enhanced Treg induction and function to maintain an atmosphere of immune tolerance to the developing fetus. As described herein, tumors may similarly elevate Activin levels. In which case, serum Activin level may be a biomarker for predicting a state of prevailing immune tolerance, predicting both patient prognosis and responsiveness to cancer vaccines and immunotherapies. Additionally, patient Activin levels may be used to justify particular immunotherapeutic treatment options (i.e., Treg and/or TGF-β depletion/inhibition).

These results support the conclusion that signaling along the Activin/ACVR1C axis can support Treg generation and function and potentially other broadly immune-suppressing effects of the TGFβ/SMAD pathway. Targeting Activin signaling is likely to undermine the tolerance promoting attributes of TGFβ and Foxp3+ Treg cells in the cancer setting—either alone, or in combination with other promising immunotherapeutic agents (e.g., immune checkpoint blocking antibodies).

Example 6

Methods and Materials

Mouse Strains

C57/BL6 Yap f/f mice were generous gifts of Dr. Duojia Pan. C57/BL6 CD4-cre and Foxp3-Cre mice were purchased from the Jackson Laboratory. Wild type C57BL/6 mice used for Activin blocking studies were provided by the NCI. All animal experiments were performed in compliance with the Johns Hopkins Animal Care and Use Policy.

In Vitro T-Cell Differentiation

Naïve CD4+ T cells (CD4+ CD25− CD62LHi) were sorted on a FACS Aria high speed sorter. The sorted cells were activated with plate-bound aCD3 (10 ug/ml) and soluble aCD28 (2ug/ml) in a 24-well plate with the following polarizing conditions: Th1 (IL-12 (10 ng/ml), aIL-4 (10 ug/ml)), Th2 (IL-4 (10 ng/ml), aIFN-g(10 ug/ml), aIL-12 (10 ug/ml)), Th17 (IL-6 (10 ng/ml), TGF-b1 (1.25 ng/ml), IL-23 (10 ng/ml), IL-1b(10 ng/ml), aIFN-g (10 ug/ml), aIL-4 (10 ug/ml), Treg (TGFb1 (5 ng/ml), IL-2 (100IU/ml).

In Vitro Suppression Assay $0.1 \times 10^6$ WT naïve CD4+ T cells were labelled with CFSE and cultured in a 96-well bottom plate with aCD3/aCD28-conjugated heads at a cell to head ratio of 1:1. Serially diluted Treg cells (CD4+ CD25Hi) were co-cultured for 72 hrs and cellular proliferation by CFSE was measured by flow cytometry.

RNASeq Analysis

Spleen and peripheral lymph nodes were harvested from YAP+/+; Foxp3-Cre-YFP+ Wild-type (WT) and YAP flox/flox (f/f); Foxp3-cre-YFP+ mice (YAP cKO) (n=5/group). CD4+ T cells were magnetically enriched, and naïve (CD4+ CD62L+ YFP−) and natural Treg (nTreg, CD4+ CD62L+/− YFP+) cells were flow sorted from each group. For activation condition, sorted nTreg cells were further activated with 2 ug/ml of plate-coated aCD3 and 2 ug/ml of soluble aCD28 with TGF-β1 (5 ng/ml) and IL-2 (100 U/ml) for 24hrs. $2 \times 10^6$ naïve or nTreg (no stimulation or stimulation) from WT and YAP cKO were harvested and washed with 1× PBS twice and immediately snap-frozen until further RNA-seq analysis.

Construction of RNA-Seq Libraries

Total RNA was isolated by TRIZOL from wild type or YAP KO naive CD4+ T cells, or YFP-Foxp3+ natural Treg cells with or without the stimulation anti-CD3/CD28 for 48 hr. RNA quality was monitored on Bioanalyzer. Strand-specific RNA-seq libraries were prepared using TruSeq Stranded Total RNA LT Sample Prep Kit (with Ribo-Zero Gold, RS-122-2301, Illumina) from 322 ng of total RNA by following manufacturer protocols. Briefly, ribosomal RNA (rRNA) in both cytoplasm and mitochondria were depleted using biotinylated, target-specific oligos combined with Ribo-Zero rRNA removal beads. After purification, the RNA was fragmented into small pieces using divalent cations under elevated temperature, which were transcribed into first strand cDNA using reverse transcriptase and random primers, followed by second strand cDNA synthesis using DNA Polymerase I and RNase H. A single "A" base was added to these cDNA fragments that were subsequently ligated with the adapter. The products were enriched with 12-cycle PCR. The concentration of final cDNA libraries in 30 ul ddH2O reached 24-27 ng/ul as determined on Qubit 2.0.

Analysis of RNA-Seq Data

Sequencing was performed on Illumina Hiseq2000 at Beijing Genomics Institute with the type of paired-end, 100 bp. The quality of sequencing data were assessed by the software FastQC (http://www.bioinformatics.babraham.ac.uk/projects/fastqc/). The mapping to mouse reference genome of mm10 was conducted by TopHat. Differentially-Expressed genes were called by Cuffdiff. The genes with p value <0.05 and absolute value of log2-transformed fold changes larger than 1/5 between wild type and YKP KO T cells were considered to be differentially expressed. Heat map was generated in R statistical software using the geom_ile function under ggplot2 package. Clustering was done with the complete linkage and euclidean distance using hclust function in R statistical software.

Flow Cytometry

For extracellular staining, harvested cells were washed and incubated in PBS containing 1% FBS containing the below fluorochrome-conjugated antibodies in a U-bottom 96-well plate. For intracellular cytokine staining, harvested cells were re-stimulated in PMA and Ionomycin in the presence of Golg-Plug (BD Biosciences). After 5 hour incubation, the cells were fixed/permeablized (eBioscience) and incubated with antibodies. IFN-g PE, IFN-g APC, IL-13 PE, IL-17 APC (BD Bioscience), IL-2 APC (BD Pharmingen), Foxp3 PE (eBioscience). For cellular proliferation, Cell Trace CFSE cell proliferation kit (Invitrogen) was used per manufacture's manual.

Quantitative Real-Time PCR

RNA was extracted using Trizol (Invitrogen) followed by cDNA synthesis reaction using SuperScript III (Invitrogen) in a 20 ul reaction/well. The same amount of RNA was used in each cDNA synthesis reaction measured by NanoDrop Spectrophotometer (ThermoScientific). The same volume of cDNA per sample was prepared for real-time PCR analysis using SYBR Green (Pierce) and the indicated primers to assess transcript levels of each gene.

B16-Melanoma Growth Experiments

B16-melanoma cells were cultured in vitro in DMEM plus 10% heat inactivated Fetal Bovine Serum and where detached by trypsinization and washed prior to s.c. injection into the footpads of C57BL/6 mice (NCI). $1-5 \times 10^4$ B16 melanoma cells were injected each mouse in the footpad. In some cases, $10^5$ B16 cells were injected. Once tumors were palpable (7-10 days), 100 ml of $1 \times 10^6$ lethally irradiated (150Gy) B16 GM-vaccine cells were injected subcutaneously into the contralateral limb. For all these experiments, 5-10 mice were used per group. Activin neutralization antibodies and isotype control IgG were purchased from R&D. 100 μg/mouse/injection of activin neutralization antibodies was given intraperitoneally twice a week. Tumor volume was determined by digital caliper measurements throughout the experiment. The relative tumor volume was calculated by the formula: Length (mm)×Width (mm)× Height (mm)×0.5326×0.01.

Example 7

Mice Lacking Activin Receptor 1C Grow Smaller Tumors

The right flank of 8 wild type (WT) and 8 Activin Receptor 1C knock out (KO) male mice were injected with 40,000 B16 tumor cells in 100 μl PBS when the mice were 8 weeks old. One WT mouse died before the end of the experiment. A photograph of excised tumors on day 22 is shown in FIG. 8A. The tumors were gently dried using tissue paper, and immediately weighed on a scale precise to 0.0001 grams. All results were graphed and analyzed using Prism 7 Software. In FIG. 8B, mean and SEM of tumor weights on day 22 are depicted (p=0.0195). The tumor length and width were measured every day (day 8 after injection until day 21). Volume was calculated using the formula (Length*Width^2)/2, where Length is the larger of the two measurements. Tumor volume means and SEMs for each day are displayed in FIG. 8C.

Equivalents

Those skilled in the art will recognize, or be able to ascertain using no more than routine experimentation, many equivalents to the specific embodiments of the invention described herein. Such equivalents are intended to be encompassed by the following claims.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating skin cancer in a subject comprising
    identifying a subject suffering from or at risk of suffering from skin cancer; and
    administering to the subject an effective amount of a composition comprising an Activin signaling antagonist that comprises an anti-ACVRIC (ALK7) antibody; thereby treating skin cancer in the subject.

2. The method of claim 1, wherein the method further comprises administering immunotherapy.

3. The method of claim 2, wherein the immunotherapy comprises a cytokine, or an immune checkpoint inhibitor.

4. The method of claim 1 wherein the subject is identified as suffering from skin cancer.

5. The method of claim 1 wherein the subject is identified as at risk of suffering from skin cancer.

6. A method of treating melanoma in a subject, comprising:
    identifying a subject suffering from or at risk of suffering from melanoma; and
    administering to the subject an effective amount of a composition comprising an Activin signaling antagonist that comprises an anti-ACVRIC (ALK7) antibody; thereby treating melanoma in the subject.

7. The method of claim 6 wherein the method further comprises administering immunotherapy.

8. The method of claim 7 wherein the immunotherapy comprises a cytokine or an immune checkpoint inhibitor.

9. The method of claim 6 wherein the subject is identified as suffering from melanoma.

10. The method of claim 6 wherein the subject is identified as at risk of suffering from melanoma.

* * * * *